US008363786B2

(12) United States Patent
Nakatsugawa et al.

(10) Patent No.: US 8,363,786 B2
(45) Date of Patent: Jan. 29, 2013

(54) RADIOGRAPHIC IMAGE CAPTURING SYSTEM

(75) Inventors: Haruyasu Nakatsugawa, Kanagawa (JP); Naoyuki Nishino, Kanagawa (JP); Yutaka Yoshida, Kanagawa (JP); Naoto Iwakiri, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 283 days.

(21) Appl. No.: 12/979,370

(22) Filed: Dec. 28, 2010

(65) Prior Publication Data

US 2011/0158385 A1 Jun. 30, 2011

(30) Foreign Application Priority Data

Dec. 28, 2009 (JP) .................................. 2009-298780
Dec. 13, 2010 (JP) .................................. 2010-277139

(51) Int. Cl.
*H05G 1/54* (2006.01)

(52) U.S. Cl. .............................. 378/116; 378/42; 378/62

(58) Field of Classification Search .................... 378/42, 378/44, 62, 98, 98.8, 101, 106, 116; 250/370.08, 250/370.09
See application file for complete search history.

(56) References Cited

U.S. PATENT DOCUMENTS

| 5,119,409 | A | 6/1992 | Nields et al. |
| 2009/0041180 | A1 | 2/2009 | Oshima |

FOREIGN PATENT DOCUMENTS

| GB | 2357953 A | 7/2001 |
| JP | 2005-323673 A | 11/2005 |
| JP | 2009-136481 A | 6/2009 |
| JP | 2009-186439 A | 8/2009 |

OTHER PUBLICATIONS

Cohen et al "Optimizing the Use of Pulsed Fluoroscopy to Reduce Radiation Exposure to Children", Journal of the American College of Radiology, Elsevier, vol. 5, No. 3, Feb. 27, 2008, pp. 205-209.

*Primary Examiner* — Courtney Thomas
(74) *Attorney, Agent, or Firm* — SOLARIS Intellectual Property Group, PLLC

(57) ABSTRACT

A radiographic image capturing system includes a radiographic image capturing device, a radiation irradiating device, and a control device. The radiographic image capturing device is capable of performing fluoroscopic imaging, and carries out capturing of radiographic images continuously. The radiation irradiating device performs continuous irradiation or pulse irradiation with respect to the radiographic image capturing device at a time of fluoroscopic imaging. The control device has a controller that affects control such that, in a case in which a frame rate of fluoroscopic imaging is low, the radiation irradiating device performs fluoroscopic imaging by the continuous irradiation with respect to the radiographic image capturing device.

11 Claims, 17 Drawing Sheets

FIG. 8

|  |  | PULSE IRRADIATION | CONTINUOUS IRRADIATION |
|---|---|---|---|
| FLUOROSCOPIC IMAGING | FRAME RATE ≧ 1ST THRESHOLD VALUE | C | C |
|  | 2ND THRESHOLD VALUE < FRAME RATE ≦ 1ST THRESHOLD VALUE | C | B |
|  | FRAME RATE ≦ 2ND THRESHOLD VALUE | D | A |
| STILL IMAGE CAPTURING |  | B | C |

A: SELECTED
B: PRIORITY LEVEL HIGH
C: PERMITTED, BUT PRIORITY LEVEL LOW
D: PROHIBITED

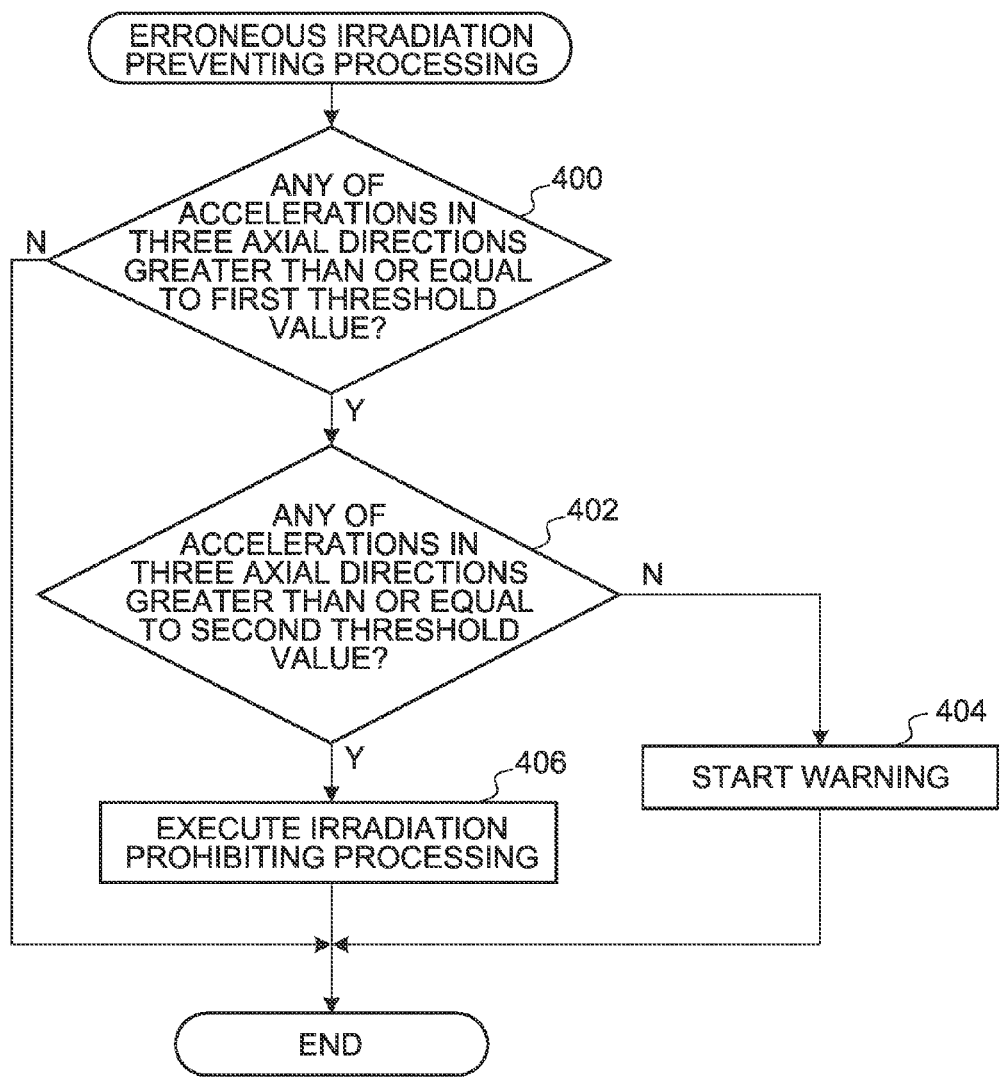

RADIOGRAPHIC IMAGE CAPTURING SYSTEM

CROSS-REFERENCE TO RELATED APPLICATION

This application claims priority under 35 USC 119 from Japanese Patent Application No. 2009-298780 filed on Dec. 28, 2009, and No. 2010-277139 filed on Dec. 13, 2010, the disclosures of which are incorporated by reference herein.

BACKGROUND OF THE INVENTION

1. Field of the Invention

The present invention relates to a radiographic image capturing system, and in particular, to a radiographic image capturing system that can carry out fluoroscopic imaging in which the capturing of radiographic images is carried out continuously.

2. Related Art

Radiation detectors such as FPDs (Flat Panel Detectors), in which a radiation-sensitive layer is disposed on a TFT (Thin Film Transistor) active matrix substrate and that can convert radiation directly into digital data have been put into practice in recent years. Portable radiographic image capturing devices (hereinafter also called "electronic cassettes"), that capture radiographic images expressed by irradiated radiation by using the radiation detector, are being put into practice. As compared with a radiographic image capturing device that uses a conventional X-ray film or imaging plate, a radiographic image capturing device that uses the radiation detector has the advantages that images can be confirmed immediately, and fluoroscopic imaging (video image capturing), in which the capturing of radiographic images is carried out continuously, also can be carried out. As methods of converting radiation at the radiation detector, there are an indirect conversion method that, after converting radiation into light at a scintillator, converts the light into charges at a semiconductor layer of photodiodes or the like, and a direct conversion method that converts radiation into charges at a semiconductor layer of amorphous selenium or the like, and the like. There exist various types of materials that can be used at the semiconductor layer in these respective methods.

As image capturing methods for fluoroscopic imaging, there are a method of capturing images at a predetermined frame rate while irradiating radiation continuously from a radiation source (continuous irradiation), and a method of, while irradiating radiation in the form of pulses synchronously with the frame rate (pulse irradiation), capturing images synchronously with the irradiation of the radiation. With pulse irradiation, the radiation can be irradiated for the time needed for imaging, and the amount of radiation that the patient is exposed to can be suppressed as compared with continuous irradiation, and there is therefore the advantage that the irradiated amount per unit time can be increased. However, with pulse irradiation, there is the need to synchronize the timing of irradiating the radiation from the radiation source and the timing of the image capturing at the radiation detector.

Japanese Patent Application Laid-Open (JP-A) No. 2009-136481 discloses a technique in which a switch for switching between continuous irradiation and pulse irradiation is provided. In imaging using C arm, when the C arm is rotated and positioning of the imaged region is carried out, the form of irradiation is switched to pulse irradiation by the switch. When capturing diagnostic images, the form of irradiation is switched to continuous irradiation by the switch, and image capturing is carried out.

JP-A No. 2009-186439 discloses, in a wireless X-ray fluoroscopic system that is physically divided into an exposure unit and a sensor unit, a technique of generating beacon signals at a period that is associated with the frame rate of image capturing, and wirelessly synchronizing the irradiation timing and the image capturing timing.

In pulse irradiation, because the irradiation time is short, the respective images become frame-advanced images having stopped motion. This trend occurs in particular in cases in which the frame rate is low, because the image capturing interval is large and after-images of the eyes also disappear.

Thus, fluoroscopic images having smooth motion may not be captured by pulse irradiation in a case in which the frame rate is low.

Note that, in the techniques of JP-A Nos. 2009-136481 and 2009-186439 as well, the capturing of fluoroscopic images having smooth motion is difficult in cases in which the frame rate is low.

SUMMARY

The present invention has been developed in consideration of the above, and provides a radiographic image capturing system that can capture fluoroscopic images having smooth motion even in cases in which the frame rate is low.

An aspect of the present invention is a radiographic image capturing system having: a radiographic image capturing device that is capable of performing fluoroscopic imaging, and that carries out capture of radiographic images continuously; a radiation irradiating device that performs continuous irradiation or pulse irradiation with respect to the radiographic image capturing device at a time of fluoroscopic imaging; and a control device having a controller that effects control such that, in a case in which a frame rate of fluoroscopic imaging is low, the radiation irradiating device performs fluoroscopic imaging by the continuous irradiation with respect to the radiographic image capturing device.

Due to this structure, fluoroscopic images having smooth motion can be captured even in cases in which the frame rate is low.

In the present aspect, the control device may further have a selection section that selects whether the radiation irradiating device performs pulse irradiation or continuous irradiation, and in a case in which a frame rate of fluoroscopic imaging is less than or equal to a first frame rate threshold value, the controller may recommend continuous irradiation rather than pulse irradiation to the selection section, and, in a case in which the frame rate of fluoroscopic imaging is less than or equal to a second frame rate threshold value that is lower than the first frame rate threshold value, the controller may prohibit selection of pulse irradiation to the selection section.

Due thereto, in a case in which the frame rate is low, fluoroscopic imaging is carried out by irradiating radiation continuously.

In the present aspect, the first frame rate threshold value may be from 15 fps to 60 fps, and the second frame rate threshold value may be from 5 fps to less than the first frame rate threshold value. According to this configuration, if the frame rate of fluoroscopic imaging is set to a level at which a person who is sensitive to flickering perceives flickering of an image, continuous irradiation is recommended, and if the frame rate is set to a level at which a large majority of people sense flickering of an image, continuous irradiation is mandatory.

More specifically, the first frame rate threshold value may be 30 fps, and the second frame rate threshold value may be 15 fps.

In the present aspect, the controller may derive an irradiated amount of radiation per one image from an irradiation time of radiation per one image at a frame rate of fluoroscopic imaging and an irradiated amount of radiation per unit time from the radiation irradiating device, and, in a case in which the derived irradiated amount of radiation per one image is less than a minimum irradiated amount that is needed for capture of radiographic images, the controller may issue a warning or change a frame rate to the frame rate at which a minimum irradiated amount per one image is obtained.

Due thereto, in a case in which the irradiated amount of radiation per one image is less than the minimum irradiated amount, a warning can be given or image capturing can be carried out by changing to a frame rate at which the minimum irradiated amount is obtained.

In the present aspect, the controller may derive the irradiated amount of radiation per unit time from the radiation irradiating device by dividing a total amount of radiation permitted for an imaged region, that is an object of image capture, by a planned image capture time.

Due thereto, even in a case in which image capturing for a planned image capture time is carried out, the total amount of radiation that is irradiated can be kept within the total amount of radiation that is permitted for the imaged region.

In the present aspect, the radiographic image capturing device may be further capable of performing still image capture, and in a case in which still image capture is to be performed, the controller may set a priority level of pulse irradiation so as to be higher than a priority level of continuous irradiation.

Due thereto, in the case of still image capture, it is possible to urge image capturing to be carried out by the priority level of pulse irradiation.

In the present aspect, the radiation irradiating device may perform continuous irradiation with a smaller radiation amount per unit time than in a case in which the radiation irradiating device performs pulse irradiation.

Due thereto, the amount of radiation to which the subject is exposed at the time of irradiating radiation continuously can be suppressed.

In the present aspect, the radiographic image capturing device may have: a radiation detector at which a plurality of pixels, that generate charges as a result of radiation being irradiated thereon and that accumulate the charge, are provided in a two-dimensional form, and that outputs the charge accumulated at the respective pixels as an electric signal; an amplifier that amplifies the electric signal output from the radiation detector; and an image capturing device controller that, in a case in which continuous irradiation is performed, carries out at least one of extending a charge accumulating time at the respective pixels so as to be longer than in pulse irradiation, increasing a gain amount of the amplifier so as to be greater than in pulse irradiation, and image processing that combines a plurality of adjacent pixels as one pixel.

Due thereto, even in cases in which fluoroscopic imaging is carried out by continuous irradiation and the amount of radiation that is irradiated per unit time is reduced, good images can be obtained.

In the present aspect, the radiographic image capturing system may further have a detecting section that detects shaking of the radiation irradiating device, wherein, in a case in which a shaking amount of the radiation irradiating device detected by the detecting section during fluoroscopic imaging is greater than or equal to a first shaking threshold value, the controller may issue a warning, and, in a case in which the shaking amount is greater than or equal to a second shaking threshold value that is greater than the first shaking threshold value, the controller may stop irradiation of radiation from the radiation irradiating device.

Due thereto, even in cases in which shaking of the radiation irradiating device arises, a warning can be given in a case in which the shaking amount is greater than the first shaking threshold value, and irradiation of the radiation can be stopped in a case in which the shaking amount is greater than the second shaking threshold value.

In the present aspect, the controller may issue the warning, and may stop irradiation of radiation, in a case in which the detecting section detects shaking of the radiation detection device during fluoroscopic imaging with continuous irradiation.

Due thereto, in a case in which shaking of the radiation irradiating device is detected in the midst of fluoroscopic imaging while irradiating radiation continuously, a warning can be given or irradiation of the radiation can be stopped, in accordance with the amount of shaking.

In accordance with the present invention, to the extent that a frame rate of fluoroscopic imaging is slow, the fluoroscopic imaging is carried out by continuously irradiating radiation from the radiation irradiating device with respect to the radiographic image capturing device. Therefore, even in cases in which the frame rate is low, fluoroscopic images having smooth motion can be captured.

BRIEF DESCRIPTION OF THE DRAWINGS

Exemplary embodiments of the present invention will be described in detail based on the following figures, wherein:

FIG. 8 is a drawing showing priority levels of continuous irradiation and pulse irradiation in fluoroscopic imaging and still image capturing relating to the exemplary embodiment;

FIG. 15 is a flowchart showing the flow of an erroneous irradiation preventing processing program relating to the exemplary embodiment;

DETAILED DESCRIPTION

Exemplary embodiments of the present invention are described in detail hereinafter with reference to the drawings. Note that, here, description is given of examples of a case in which the present invention is applied to a radiology information system that is a system that all-inclusively manages information that is handled in the radiology department of a hospital.

Figure 1:
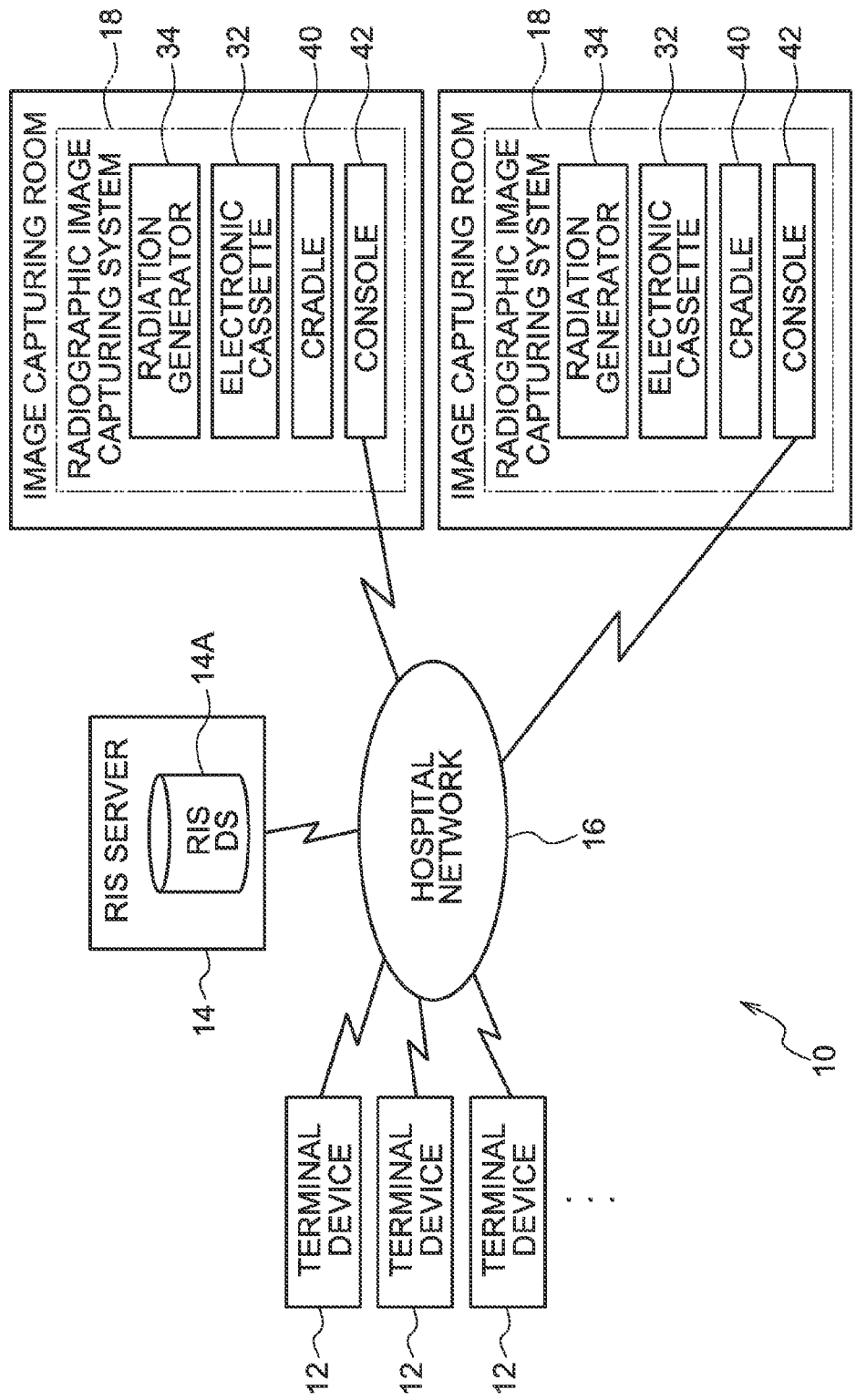
FIG. 1 is a block diagram showing the structure of a radiology information system relating to an exemplary embodiment.

Firstly, a configuration of a radiology information system 10 (which will be called "the RIS 10" below) of the present embodiment will be described in reference to FIG. 1.

The RIS 10 is a system for managing information such as medical service appointments and diagnostic records in a radiology department and configures part of a hospital information system (HIS).

The RIS 10 includes plural image capture request terminals 12 (which will be called "the terminals 12" below), RIS server 14 and radiographic image capturing systems 18 (hereinafter, referred to as "capturing systems") installed in individual radiographic image capturing rooms (or operating rooms) in a hospital being connected to a hospital network 16 that is structured by a wired or wireless local area network (LAN). The RIS 10 serves as part of the HIS that is disposed in the same hospital, and an HIS server (not shown) that manages the entire HIS is also connected to the hospital network 16.

The terminals 12 are devices for doctors or radiologic technologists to input/browse diagnostic information and facility reservations, and requests to capture radiographic images or image capture reservations are also performed from the terminals 12. Each of the terminals 12 is configured by a personal computer equipped with a display device, and the terminals 12 are connected by the hospital network 16 to the RIS server 14 so as to be capable of communicating with each other.

The RIS server 14 receives the image capture requests from the terminals 12, manages radiographic image capture schedules in the image capturing systems 18, and includes a database 14A.

The database 14A stores information (data) relating to a patient, such as attribute information (name, sex, date of birth, age, blood type, weight, patient ID (identification) and the like) of the patient, medical history, consultation history, and radiographic images captured in the past.

The image capturing systems 18 capture radiographic images by operation of the doctors or radiologic technologists in response to an instruction from the RIS server 14. Each of the capturing systems 18 is equipped with a radiation generator 34 that irradiates a subject with radiation X (see also FIG. 3) from a radiation source 130 (see also FIG. 2) of a radiation amount corresponding to image capture conditions, an electronic cassette 32 that includes a radiation detector 60 (see also FIG. 3) that absorbs the radiation X that has been transmitted through an image capture area of the patient and generates charges, and generates image information representing radiographic image information (data) based on the generated charge amount, a cradle 40 that charges a battery built into the electronic cassette 32, and a console 42 that controls the electronic cassette 32, the radiation generator 34, and the cradle 40.

Figure 2:
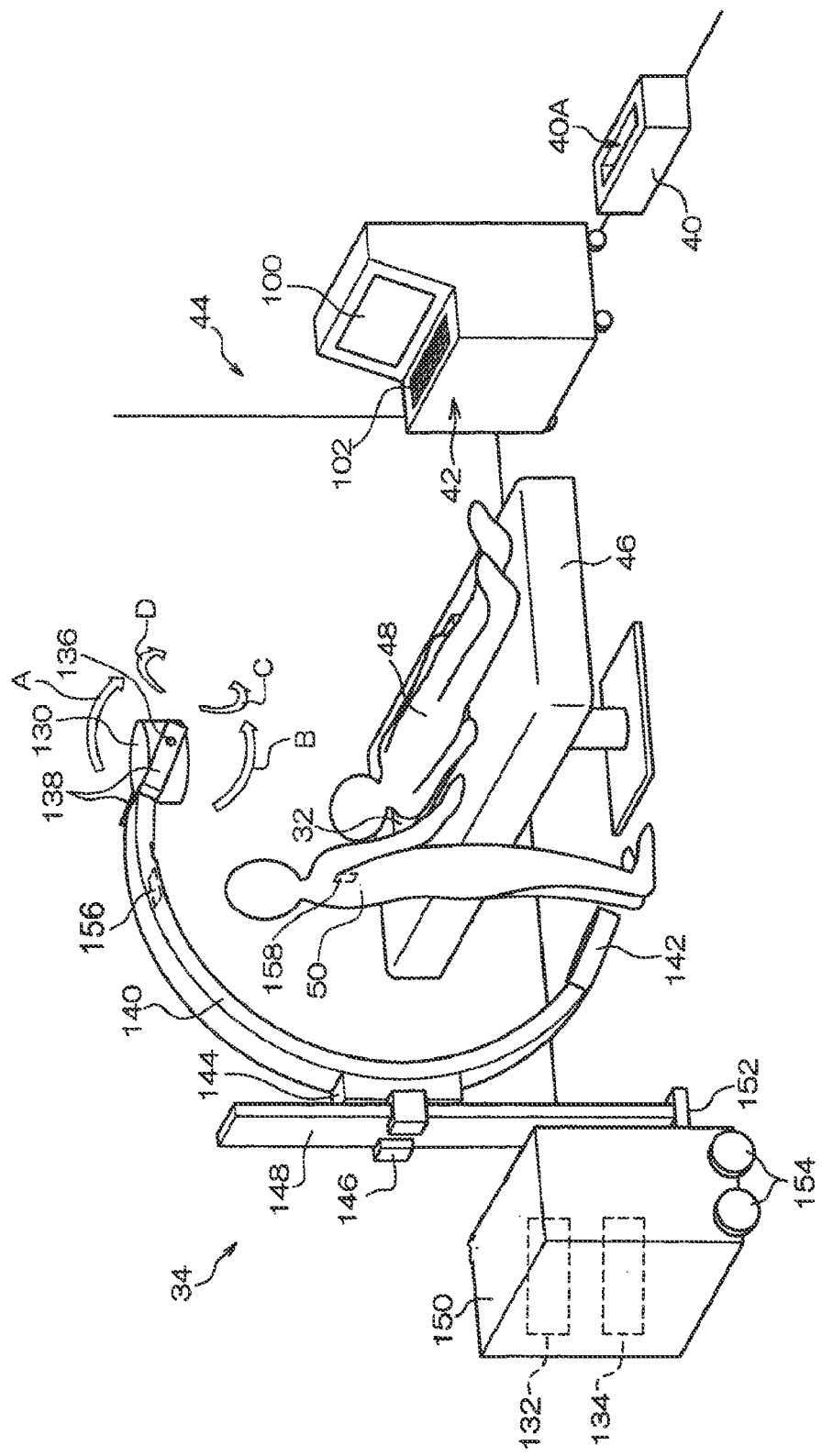
FIG. 2 is a perspective view showing an example of the state of placement of respective devices in a radiographic image capturing room of a radiographic image capturing system relating to the exemplary embodiment, and the structure of a radiation generator.

FIG. 2 shows an example of the arrangements of the image capturing systems 18 in an radiographic image capturing room 44 and a configuration of the radiation generator 34 according to the present exemplary embodiment. In the image capturing system 18, the console 42 is mutually connected to the radiation generator 34 such that these devices transmit and receive various types of information by wired communication, but in FIG. 2, the cables that interconnect these devices are omitted. Further, the electronic cassette 32 and the console 42 may transmit and receive various types of information by wired or wireless communication.

The radiation generator 34 relating to the present exemplary embodiment has a C arm 140. The radiation source 130 that emits radiation X is provided at one end of the C arm 140. An attachment structure 142, to and from which the electronic cassette 32 can be attached and removed, is provided at the other end of the C arm 140. Note that FIG. 2 shows a state in which the electronic cassette 32 is removed from the attachment structure 142 and is provided between a bed 46, that is provided at the substantially central portion of the radiographic image capturing room 44, and a subject (patient) 48 who is lying on the bed 46.

The radiation source 130 is provided at one end of the C arm 140 via a supporting shaft 136 and a pair of supporting plates 138. The radiation source 130 can be rotated in direction A and direction B in FIG. 2 around the supporting shaft 136, and can be rotated together with the supporting plates 138 in direction C and direction D in FIG. 2 around a tangent line of the arc of the C arm 140.

A C arm holding portion 144, that holds the C arm 140 such that the C arm 140 can rotate clockwise and counterclockwise in FIG. 2, is provided at a position that abuts the outer periphery of the cylindrical surface of the C arm 140. The C arm holding portion 144 is held, via a C arm holding portion 146, at a support 148 so as to freely move vertically. Further, the C arm holding portion 144 is supported so as to be able to rotate around a horizontal axis with respect to the C arm holding portion 146.

The radiation generator 34 has a main body 150 that incorporates therein a communication interface 132, a radiation source controller 134, and the like that are described below. The lower end of the support 148 is mounted to a support supporting section 152 that projects-out to the side from a vicinity of the lower end portion of the housing of the main body 150.

Wheels 154 are provided at the bottom portion of the main body 150, such that the radiation generator 34 can move within the hospital.

The cradle 40 and the console 42 are set in a vicinity of a wall surface in the radiographic image capturing room 44 relating to the present exemplary embodiment.

A housing portion 40A that can house the electronic cassette 32 is formed in the cradle 40.

When the electronic cassette 32 stands by, the electronic cassette 32 is housed in the housing portion 40A of the cradle 40 and the built-in battery is charged, and when a radiographic image is to be captured, the electronic cassette 32 is removed from the cradle 40 and disposed in the area of the patient 30 of which an image is to be captured, or mounted on the attachment structure 142 of the C arm 140 of the radiation generator 34.

The electronic cassette 32 is not limited to being used in the operating room 44 and can also be applied to medical screenings and rounds inside a hospital, for example.

Figure 3:
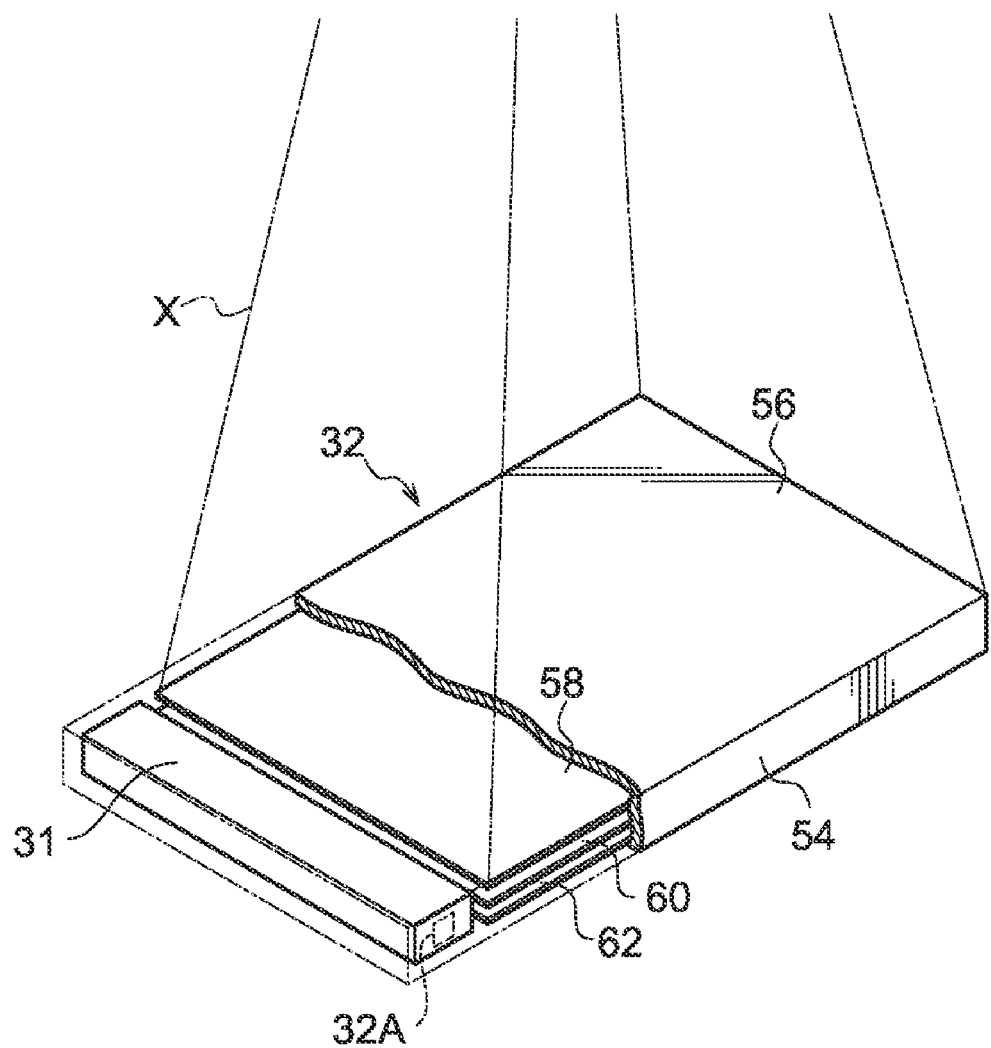
FIG. 3 is a transparent perspective view showing the internal structure of an electronic cassette relating to the exemplary embodiment.

FIG. 3 shows the internal configuration of the electronic cassette 32 pertaining to the exemplary embodiment.

As shown in FIG. 3, the electronic cassette 32 is equipped with a casing 54 formed by a material that allows the radiation X to be transmitted therethrough, and the electronic cassette 32 is configured to have a waterproof and hermetic structure. There is the fear that blood or other contaminant may adhere to the electronic cassette 32 when the electronic cassette 32 is used in an operating room or the like. Thus, the electronic cassette 32 is configured to have a waterproof and hermetic structure and is washed with an antiseptic as needed, so that the one electronic cassette 32 can be used repeatedly.

Inside the casing 54, there are disposed, in order from an irradiated surface 56 side of the casing 54 that is irradiated with the radiation X, a grid 58 that removes scattered radiation of the radiation X resulting from the patient, the radiation detector 60 that detects the radiation X that has been transmitted through the patient, and a lead plate 62 that absorbs back scattered radiation of the radiation X. The irradiated surface 56 of the casing 54 may also be configured by the grid 58. A connection terminal 32A for connecting a cable 43 is provided at a side of the casing 54.

A case 31 that houses electronic circuits including a microcomputer and a rechargeable secondary battery is disposed on one end side of the inside of the casing 54. The radiation detector 60 and associated electronic circuits are actuated by power supplied from the secondary battery disposed in the case 31. A lead plate or the like may be disposed on the irradiated surface 56 side of the case 31 in order to avoid a situation where the various circuits housed inside the case 31 sustain damage in accompaniment with being irradiated with the radiation X. In the present exemplary embodiment, the electronic cassette 32 is configured as a rectangular parallelepiped in which the irradiated surface 56 is formed in a rectangle shape, and the case 31 is disposed at one side in a longitudinal direction of the rectangular parallelepiped.

Figure 4:
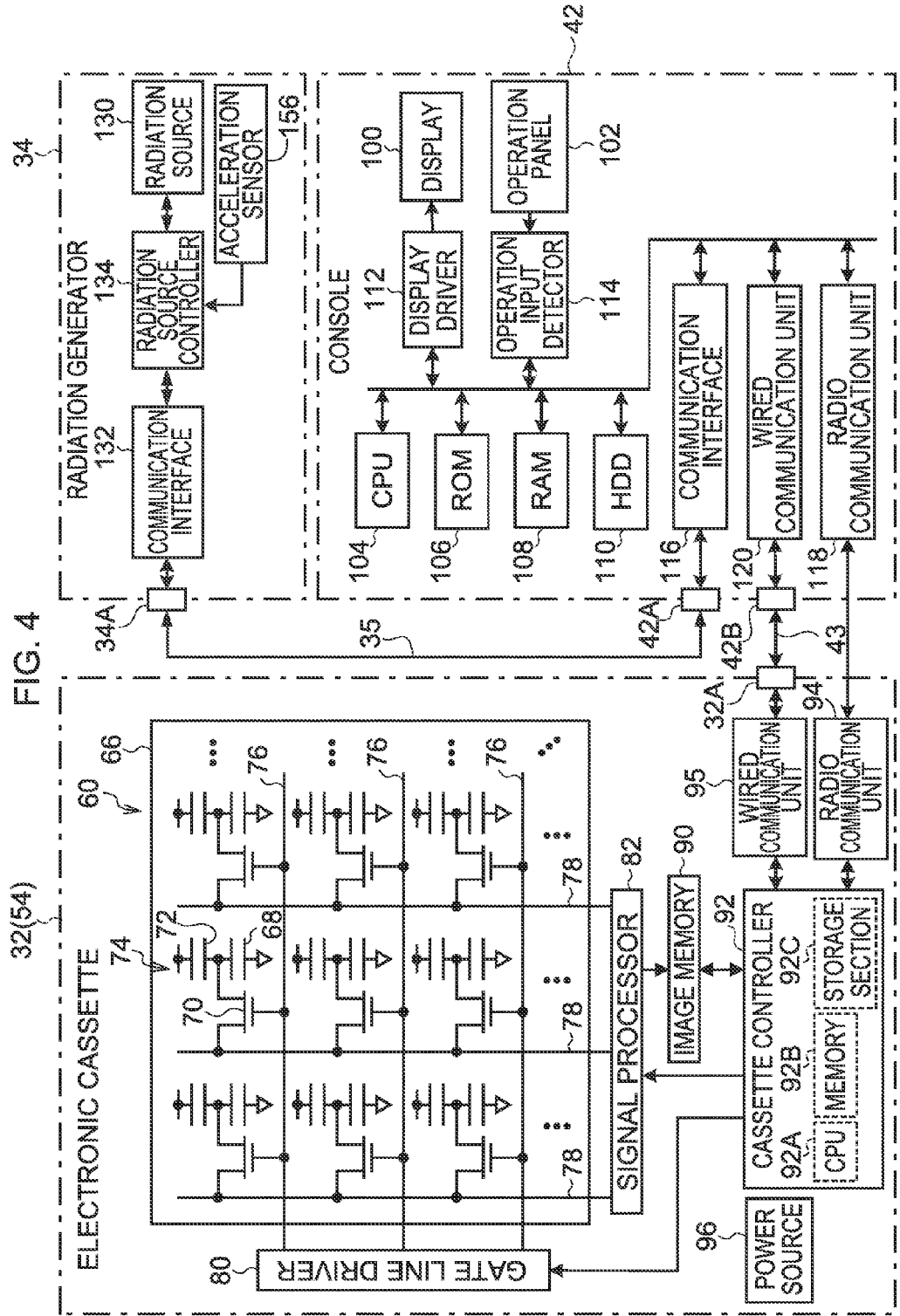
FIG. 4 is a block diagram showing the structures of main portions of the electrical system of the image capturing system relating to the exemplary embodiment.

FIG. 4 shows a block diagram showing the detailed configuration of the radiographic image capturing system 18.

A connection terminal 34A for performing communication with the console 42 is disposed in the radiation generator 34. A connection terminal 42A for performing communication with the radiation generator 34, a connection terminal 42B for performing communication with the electronic cassette 32 are disposed in the console 42. The connection terminal 34A of the radiation generator 34 and the connection terminal 42A of the console 42 are connected with a cable 35.

When the electronic cassette 32 performs wired communication, the cable 43 is connected to the connection terminal 32A and the electronic cassette 32 is connected to the console 42 via the cable 43.

The radiation detector 60 built into the electronic cassette 32 is configured by a photoelectric conversion layer that absorbs and converts the radiation X into electric charges being layered on a TFT active matrix substrate 66. The photoelectric conversion layer contains, for example, amorphous selenium (a-Se) whose main component (e.g., having a content percentage equal to or greater than 50%) is selenium, and when the photoelectric conversion layer is irradiated with the radiation X, the photoelectric conversion layer converts the radiation X which has been irradiated into electric charges by generating, inside itself, electric charges (electron-hole pairs) of an electric charge amount corresponding to the amount of the radiation X which has been irradiated. The radiation detector 60 may also, instead of a material that directly converts the radiation X into electric charges such as amorphous selenium, use a fluorescent material and a photoelectric conversion element (photodiode) to indirectly convert the radiation X into electric charges. As the phosphor material, gadolinium oxysulfide (GOS) and cesium iodide (CsI) are known. In this case, conversion of the radiation X into light is performed by the fluorescent material, and conversion of the light into electric charges is performed by the photodiode of the photoelectric conversion element.

Further, on the TFT active matrix substrate 66, numerous pixels 74 (in FIG. 4, the photoelectric conversion layer corresponding to the individual pixels 74 is schematically shown as photoelectric converters 72) equipped with storage capacitors 68 that store the electric charges that have been generated by the photoelectric conversion layer and TFTs 70 for reading the electric charges that have been stored in the storage capacitors 68 are arranged in a matrix. The electric charges that have been generated in the photoelectric conversion layer by the irradiation of the electronic cassette 32 with the radiation X are stored in the storage capacitors 68 of the individual pixels 74. Thus, the image information that had been carried in the radiation X with which the electronic cassette 32 was irradiated is converted into electric charge information (an amount of electric charge) and is held in the radiation detector 60.

Further, on the TFT active matrix substrate 66, there are disposed plural gate lines 76, which extend in one direction (row direction) and are for switching ON and OFF the TFTs 70 of the individual pixels 74, and plural data lines 78, which extend in a direction (column direction) orthogonal to the gate lines 76 and are for reading the stored electric charges from the storage capacitors 68 via the TFTs 70 that have been switched ON. The individual gate lines 76 are connected to a gate line driver 80, and the individual data lines 78 are connected to a signal processor 82. When the electric charges are stored in the storage capacitors 68 of the individual pixels 74, the TFTs 70 of the individual pixels 74 are switched ON in order in row units by signals that are supplied via the gate lines 76 from the gate line driver 80. The electric charges that are stored in the storage capacitors 68 of the pixels 74 whose TFTs 70 have been switched ON are transmitted through the data lines 78 as electric charge signals and are inputted to the signal processor 82. Consequently, the electric charges that are stored in the storage capacitors 68 of the individual pixels 74 are read in order in row units.

Figure 5:
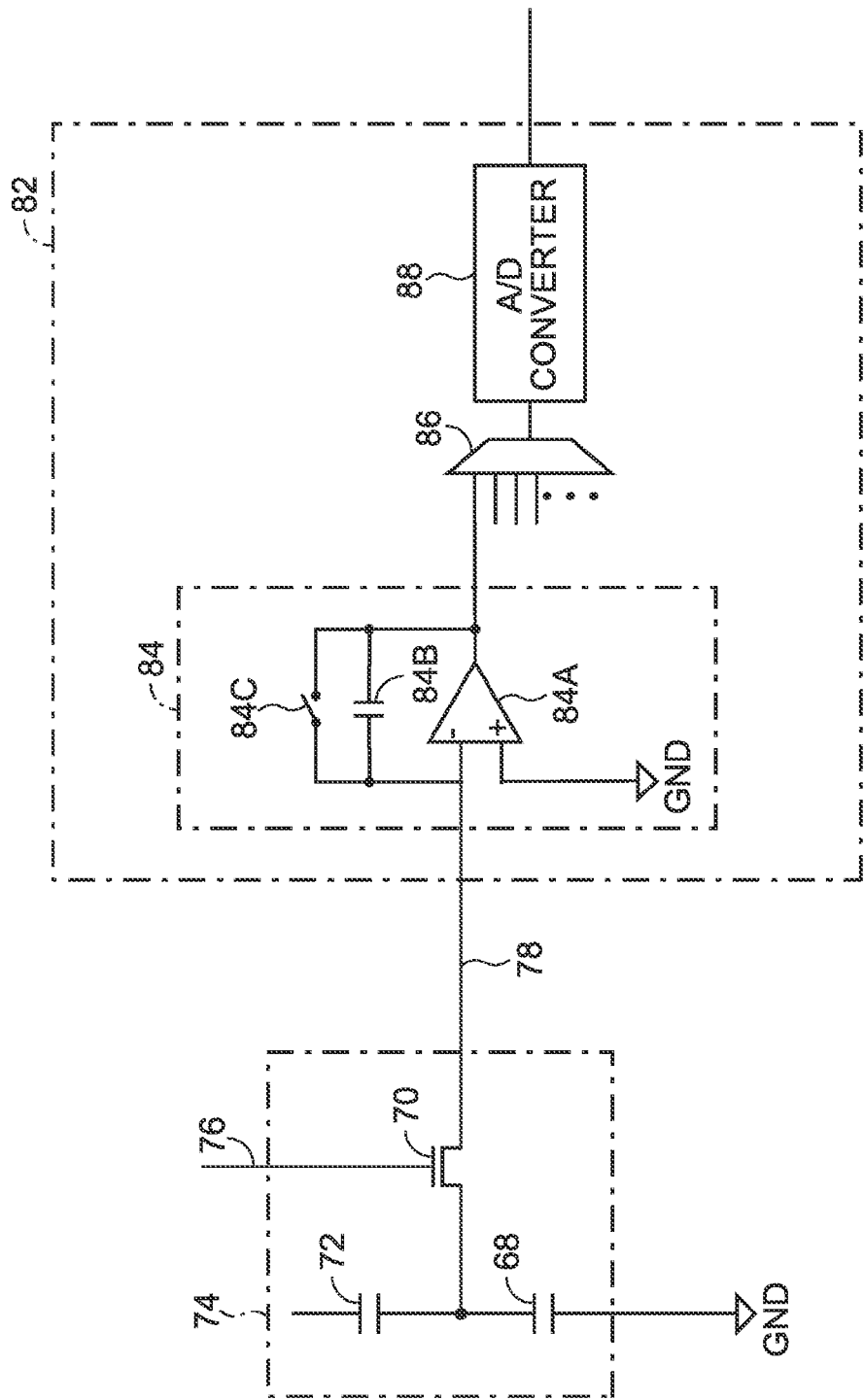
FIG. 5 is an equivalent circuit diagram that focuses on one pixel portion of a radiation detector relating to the exemplary embodiment.

FIG. 5 shows an equivalent circuit diagram focusing on one pixel portion of the radiation detector 60 pertaining to the exemplary embodiment.

As shown in FIG. 5, a source of the TFT 70 is connected to the data line 78, and the data line 78 is connected to the signal processor 82. Further, a drain of the TFT 70 is connected to the storage capacitor 68 and to the photoelectric converter 72, and a gate of the TFT 70 is connected to the gate line 76.

The signal processor 82 is equipped with a sample/hold circuit 84 for each of the individual data lines 78. The electric charge signals that have been transmitted through the individual data lines 78 are held in the sample/hold circuits 84. The sample/hold circuit 84 includes an operational amplifier (op-amp) 84A and a capacitor 84B and converts the electric charge signal into an analog voltage. Further, a switch 84C, which serves as a reset circuit that causes both electrodes of the capacitor 84B to short to cause the electric charge stored in the capacitor 84B to be discharged as a result of the switch 84C being switched ON, is disposed in the sample/hold circuit 84. The gain amount of the operational amplifier 84A can be adjusted by control of a cassette controller 92 which will be described later.

A multiplexer 86 and an analog/digital (A/D) converter 88 are connected in this order at an output side of the sample/hold circuits 84. The electric charge signals held in the individual sample/hold circuits 84 are converted into analog voltages, and the analog voltages are inputted in order (serially) to the multiplexer 86 and converted into digital image data by the A/D converter 88.

An image memory 90 is connected to the signal processor 82 (see FIG. 4). The image data that have been outputted from the A/D converter 88 of the signal processor 82 are stored in order in the image memory 90. The image memory 90 has a storage capacity that is capable of storing plural frames' worth of image data representing a radiographic image, and each time capturing of a radiographic image is performed, image data obtained by the capturing is sequentially stored in the image memory 90.

The image memory 90 is connected to the cassette controller 92 that controls operation of the entire electronic cassette 32. The cassette controller 92 is realized by a microcomputer, and includes a central processing unit (CPU) 92A, a memory 92B including a read only memory (ROM) and a random access memory (RAM), and an non-volatile storage section 92C that may formed of a hard disk drive (HDD), flash memory or the like.

A radio communication unit 94 and a wired communication unit 95 are connected to the cassette controller 92. The radio communication unit 94 is adapted to a wireless local area network (LAN) specification represented by for example IEEE (Institute of Electrical and Electronics Engineers) 802.11a/b/g and controls the transmission of various types of information between the electronic cassette 32 and an external device by radio communication. The wired communication unit 95 is connected to the connection terminal 32A and controls the transmission of various types of various types of information between the electronic cassette 32 and the console 42 via the connection terminal 32A and the cable 43. The cassette controller 92 can perform communication with the console 42 via the radio communication unit 94 or the wired communication unit 95, and transmits various types of information to and receives various types of information from the console 42 via the radio communication unit 94 or the wired communication unit 95. The cassette controller 92 stores exposure conditions received via the radio communication unit 94 or the wired communication unit 95, which will be described later, and starts reading out of charges based on the exposure conditions.

A power source 96 is provided in the electronic cassette 32, and the various circuits and elements mentioned above (such as the gate line driver 80, the signal processor 82, the image memory 90, the radio communication unit 94, the wired communication unit 95, and the microcomputer that functions as the cassette controller 92) are actuated by power supplied from the power source 96. The power source 96 has a built-in battery (a rechargeable secondary battery) so as to not impair the portability of the electronic cassette 32, and the power source 96 supplies power to the various circuits and elements from the charged battery. In FIG. 4, wirings connecting the various circuits and elements and the power source 96 are omitted.

The console 42 is configured as a server computer and is equipped with a display 100, which displays operation menus and radiographic images that have been captured, and an operation panel 102, which includes plural keys and by which various types of information and operation instructions are inputted.

Further, the console 42 pertaining to the exemplary embodiment is equipped with a central processing unit (CPU) 104 that controls operation of the entire device, a read-only memory (ROM) 106 in which various programs including a control program are stored beforehand, a random-access memory (RAM) 108 that temporarily stores various types of data, a hard disk drive (HDD) 110 that stores and maintains various types of data, a display driver 112 that controls the display of various types of information on the display 100, and an operation input detector 114 that detects states of operation with respect to the operation panel 102. The console 42 further includes a communication interface 116 that is connected to the connection terminal 42A and transmits various types of information to and receives various types of information from the radiation generator 34 via the connection terminal 42A and the cable 35 such as the exposure conditions which will be described later, a radio communication unit 118 that transmits various types of information to and receives various types of information from the radiation generator 34 such as the exposure conditions, and a wired communication unit 120 that is connected to the connection terminal 42B and transmits various types of information to and receives various types of information from the electronic cassette 32 such as image data via the connection terminal 42B and the cable 43.

The CPU 104, the ROM 106, the RAM 108, the HDD 110, the display driver 112, the operation input detector 114, the communication interface 116, the radio communication unit 118, and the wired communication unit 120 are interconnected via a system bus BUS. Consequently, the CPU 104 can access the ROM 106, the RAM 108 and the HDD 110, can control the display of various types of information on the display 100 via the display driver 112, can control the transmission of various types of information to and the reception of various types of information from the radiation generator 34 via the communication interface 116, can control the transmission of various types of information to and the reception of various types of information from the electronic cassette 32 via the radio communication unit 118, and can control the transmission of various types of information to and the reception of various types of information from the electronic cassette 32 via the wired communication unit 120. Further, the CPU 104 can grasp states of operation by a user with respect to the operation panel 102 via the operation input detector 114.

The radiation generator 34 is equipped with the radiation source 130 that outputs the radiation X, a communication interface 132 that transmits various types of information to and receives various types of information from the console 42 such as exposure conditions, and a radiation source controller 134 that controls the radiation source 130 on the basis of received exposure conditions.

The radiation source controller 134 is also realized by a microcomputer, stores the received exposure conditions, and causes the radiation source 130 to irradiate the radiation X on the basis of the stored exposure conditions.

An acceleration sensor 156 is provided at the radiation generator 34 relating to the present exemplary embodiment in a vicinity of the position where the radiation source 130 is set at the C arm 140 as shown in FIG. 2, in order to prevent failures in the capturing of radiographic images caused by some object contacting or colliding with the radiation source 130. In the present exemplary embodiment, the acceleration sensor 156 is a sensor that senses the way of application of velocity with respect to three axial directions that are the vertical direction, the left-right direction and the front-back direction. The acceleration sensor 156 may be any type provided that it can detect acceleration, and may be, for example, a piezoresistance type sensor or an electrostatic capacity type sensor.

As shown in FIG. 4, the acceleration sensor 156 is connected to the radiation source controller 134. Signals, that are outputted from the acceleration sensor 156 and express the accelerations in the three axial directions, are inputted to the radiation source controller 134. The radiation source controller 134 transmits the acceleration information, that is inputted from the acceleration sensor 156 and expresses the accelerations in the three axial directions, to the console 42 via the communication interface 132.

Next, overall operation of the capturing system 18 pertaining to the exemplary embodiment will be described.

The electronic cassette 32 and the console 42 pertaining to the exemplary embodiment perform wired communication when they are interconnected by the communication cable 43 and perform radio communication when they are not interconnected by the communication cable 43.

The capturing system 18 of the present exemplary embodiment is configured to be capable of selecting a capturing mode from still image capturing that performs capturing one by one, or fluoroscopic imaging that performs capturing continuously. Further, the capturing system 18 is configured to be capable of selecting continuous irradiation in which radiation is continuously irradiated from the radiation source 130 during the capturing or pulse irradiation in which radiation is irradiated in pulsed form from the radiation source 130 in synchronization with the frame rate of the capturing during the capturing.

One of the terminals 12 (see FIG. 1) receives an image capture request from a doctor or a radiologic technologist. In the image capture request, there are designated a patient to be captured, the area of the patient to be captured, the capturing more, and optionally the tube voltage, the tube current, the irradiation time, and the total radiation amount.

The terminal 12 notifies the RIS server 14 of the content of the received image capture request. The RIS server 14 stores, in the database 14A, the content of the image capture request which has been notified by the terminals 12.

The console 42 accesses the RIS 14 to acquire the content of the image capture request and the attribute information (data) of a patient to be captured from the RIS server 14 and display the content of the image capture request and the attribute data of the patient on the display 100 (see FIG. 4).

An operator initiates capture of a radiographic image on the basis of the content of the image capture request displayed on the display 100.

For example, as shown in FIG. 2, when capture of a radiographic image of an affected area of a subject 48 lying on the bed 46 is to be performed, the operator disposes the electronic cassette 32 between the bed 46 and the affected area of the subject 48 in accordance with the area of image capture, without connecting the cable 43 to the electronic cassette 32 and the console 42 in case of using radio communication, or after connecting the electronic cassette 32 and the console 42 with the cable 43.

Then, at the operation panel 102, the operator designates still image capturing or fluoroscopic imaging as the image capturing mode. In a case in which still image capturing is designated as the image capturing mode, the operator designates, at the operation panel 102, the exposure conditions such as the tube voltage, tube current, irradiation time, and the like for the time when the radiation X is irradiated. In a case in which fluoroscopic imaging is designated as the image capturing mode, the operator designates, at the operation panel 102, the exposure conditions such as the frame rate, the tube voltage, the tube current, and the like.

Further, the operator designates by which of continuous irradiation or pulse irradiation the image capturing is to be carried out.

Figure 6A:
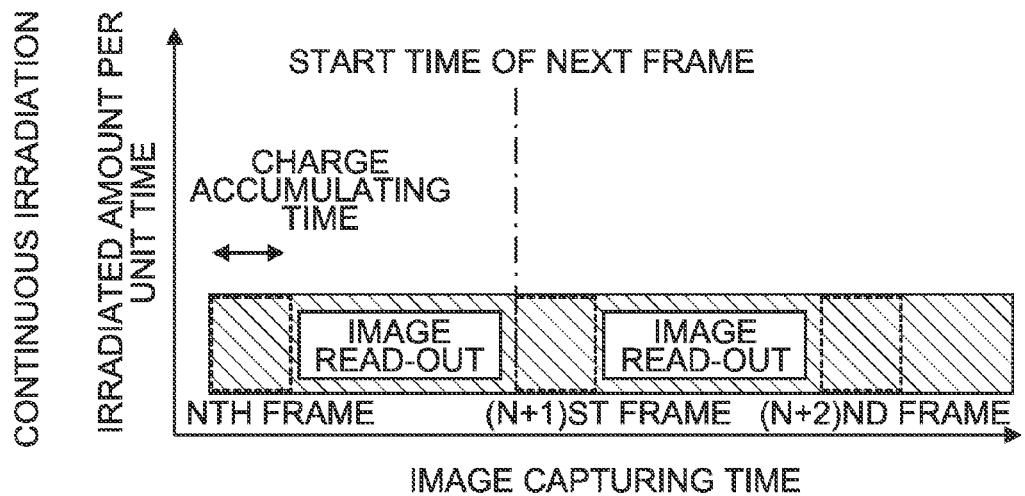
FIGS. 6A and 6B are time charts showing irradiation times of radiation by continuous irradiation and pulse irradiation, irradiated amounts of radiation per unit time, and image readout timings, relating to the exemplary embodiment.

As shown in FIG. 6A, in continuous irradiation, radiation is irradiated continuously, and radiation is irradiated also at the time of image read-out. Therefore, there is the need to keep the irradiated amount of radiation per unit time low and suppress the amount of radiation that the subject 48 is exposed to.

Figure 6B:
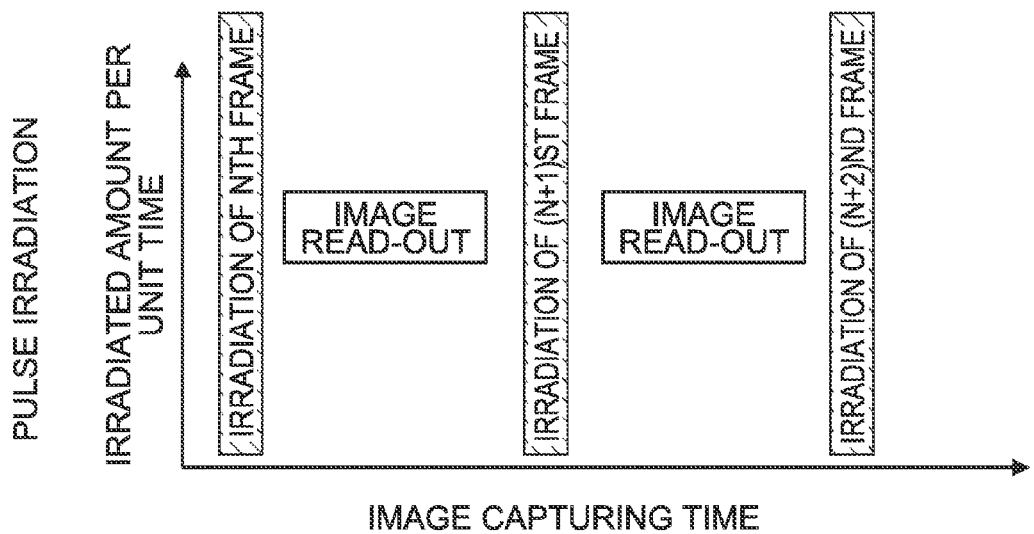

However, as shown in FIG. 6B, in pulse irradiation, radiation can be irradiated for the time period needed for image capturing, and the amount of radiation that the patient is exposed to can be suppressed as compared with continuous irradiation. Therefore, pulse irradiation has the advantage that the irradiated amount per unit time is increased.

Therefore, in the present exemplary embodiment, in a case in which continuous irradiation of radiation is carried out, the ranges over which the tube voltage and the tube current can be designated from the operation panel 102 are limited so that the irradiated radiation amount per unit time is reduced as compared with a case in which pulse irradiation of radiation is carried out. The amount of radiation to which the subject is exposed at the time of continuous irradiation can thereby be suppressed.

In pulse irradiation, because the irradiation time is short, the respective images may become frame-advanced images having stopped motion. In particular, in cases in which the frame rate is low, the image capturing interval is large and after-images of the eyes also disappear, and therefore, fluoroscopic images having smooth motion cannot be captured.

In contrast, with continuous irradiation, radiation is irradiated continuously, and after-images due to motion of an object that moves are also recorded in the radiographic images. Therefore, even in cases in which the frame rate is slow, fluoroscopic images having smooth motion can be captured.

In the present exemplary embodiment, in order to judge which irradiation mode among continuous irradiation and pulse irradiation should be given priority, frame rate threshold values are stored in advance in the HDD 110, and the irradiation mode to be prioritized is judged by comparing the frame rate of the fluoroscopic imaging with the threshold values. The time resolution of a human eye is around 50 ms to 100 ms, and flashing of light that is shorter than this time is perceived as continuous lighting. In the present exemplary embodiment, two frame rate threshold values (a first frame rate threshold value and a second frame rate threshold value) are stored. The first frame rate threshold value may be a frame rate at which a large majority of people do not sense flickering. Specifically, the first frame rate threshold value may be from 15 fps (frames per second) to 60 fps, and more preferably, from 15 fps to 30 fps. The second frame rate threshold value may be a frame rate at which a large majority of people sense flickering. Specifically, the second frame rate threshold value may be from 5 fps to less that the first frame rate threshold value, and more preferably, from 5 fps to less than 15 fps. In the present exemplary embodiment, for example, the first frame rate threshold value is set to 30 fps and the second frame rate threshold value is set to 15 fps. However, embodiments are not limited to this and, for example, the first frame rate threshold value may be 24 fps and the second frame rate threshold value may be 5 fps.

Figure 7:
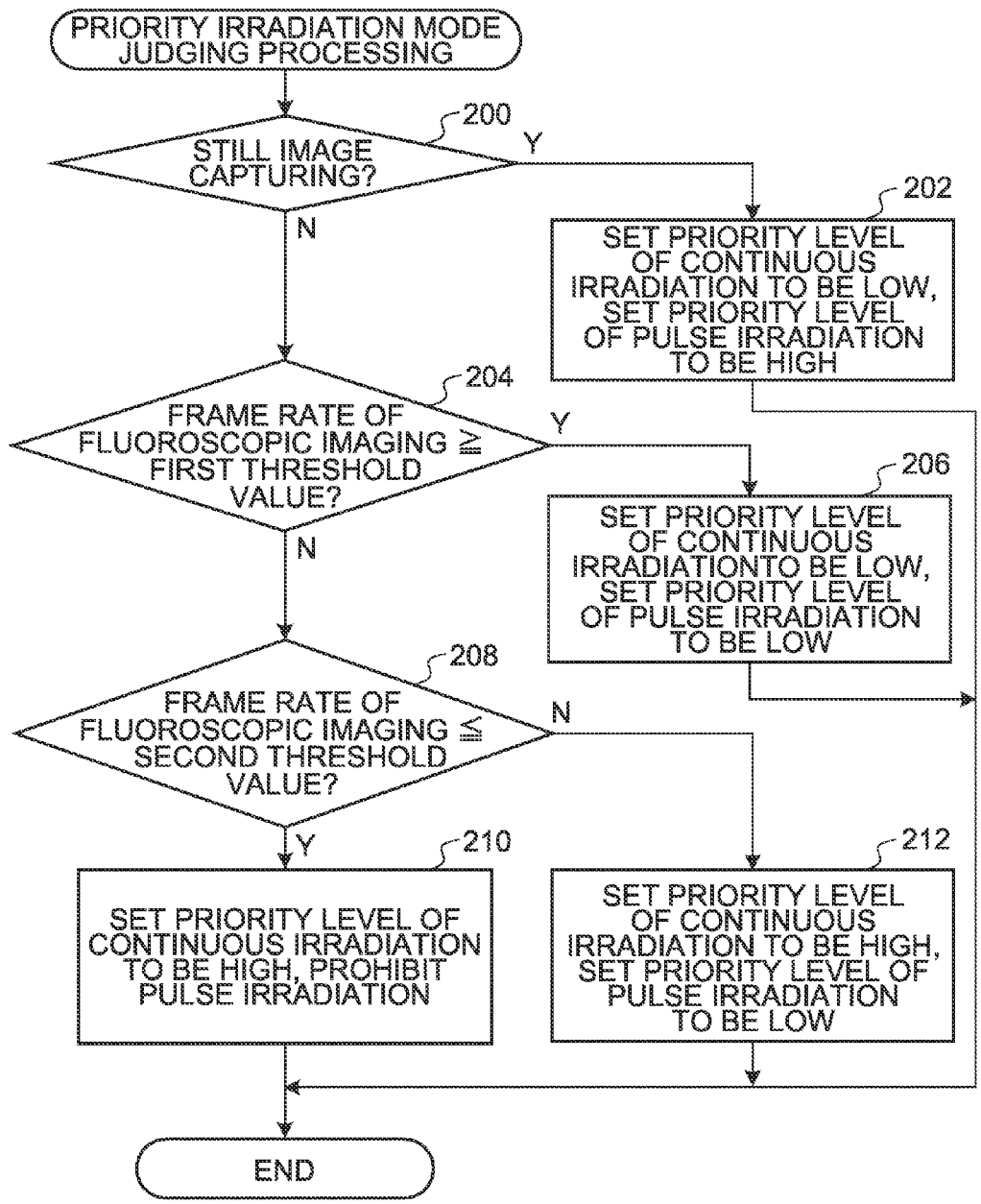
FIG. 7 is a flowchart showing the flow of a priority irradiation mode judging processing program relating to the exemplary embodiment.

FIG. 7 is a flowchart showing the flow of processings of a priority irradiation mode judging processing program that is executed at the CPU 104 relating to the present exemplary embodiment. This program is stored in advance in a predetermined area of the HDD 110, and is executed when a designating operation, that designates the image capturing mode and the exposure conditions, is carried out with respect to the operation panel 102.

In step 200 of FIG. 7, judgment is made as to whether or not the designated image capturing mode is still image capturing. If the judgment is affirmative, the routine moves on to step 202. If the judgment is negative, the routine proceeds to step 204.

In step 202, the priority level of continuous irradiation is set low, the priority level of pulse irradiation is set high, and the present priority irradiation mode judging processing program ends.

In step 204, judgment is made as to whether or not the frame rate of the fluoroscopic imaging is greater than or equal to the first frame rate threshold value (e.g., 30 fps). If the judgment is affirmative, the routine moves on to step 206, whereas if the judgment is negative, the routine moves on to step 208.

In step 206, the priority levels of continuous irradiation and pulse irradiation are set low, and the present priority irradiation mode judging processing program ends.

In step 208, judgment is made as to whether or not the frame rate of the fluoroscopic imaging is less than or equal to the second frame rate threshold value (e.g., 15 fps). If the judgment is affirmative, the routine moves on to step 210, whereas if the judgment is negative, the routine proceeds to step 212.

In step 210, pulse irradiation is prohibited, the priority level of continuous irradiation is set high, and the present priority irradiation mode judging processing program ends.

In step 212, the priority level of pulse irradiation is set low, the priority level of continuous irradiation is set high, and present priority irradiation mode judging processing program ends.

Due thereto, as shown in FIG. 8, in a case in which the image capturing mode is still image capturing, the priority level of continuous irradiation is low, and the priority level of pulse irradiation is high. In a case in which the image capturing mode is fluoroscopic imaging, the priority levels of continuous irradiation and pulse irradiation are determined in accordance with the frame rate of the fluoroscopic imaging.

Figure 9A:
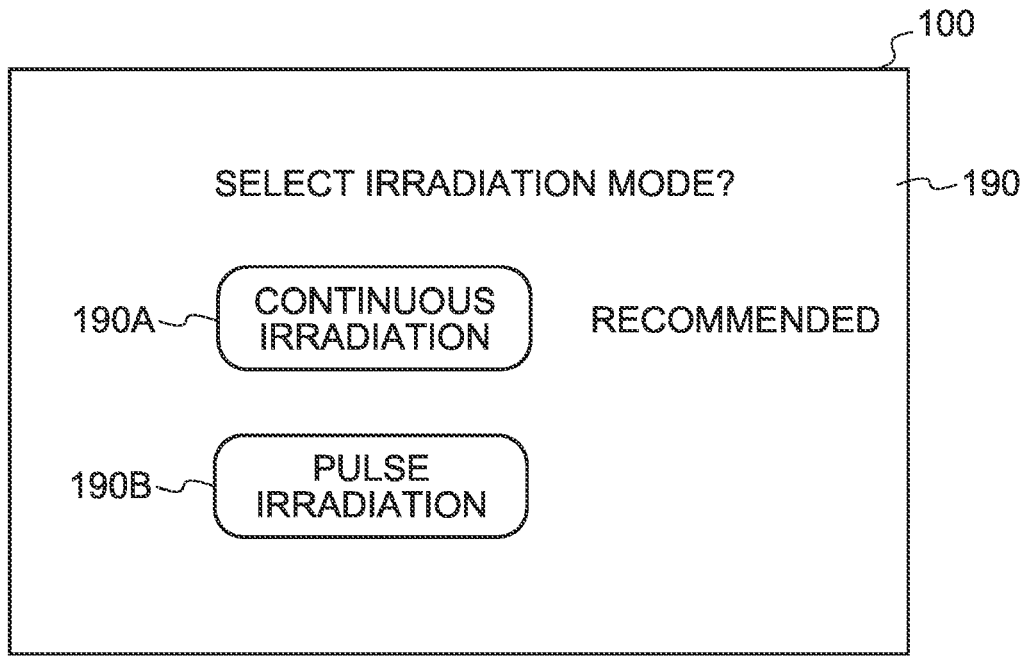
FIGS. 9A and 9B are schematic drawings showing examples of a selection screen that enables selection of continuous irradiation or pulse irradiation relating to the exemplary embodiment.
Figure 9B:
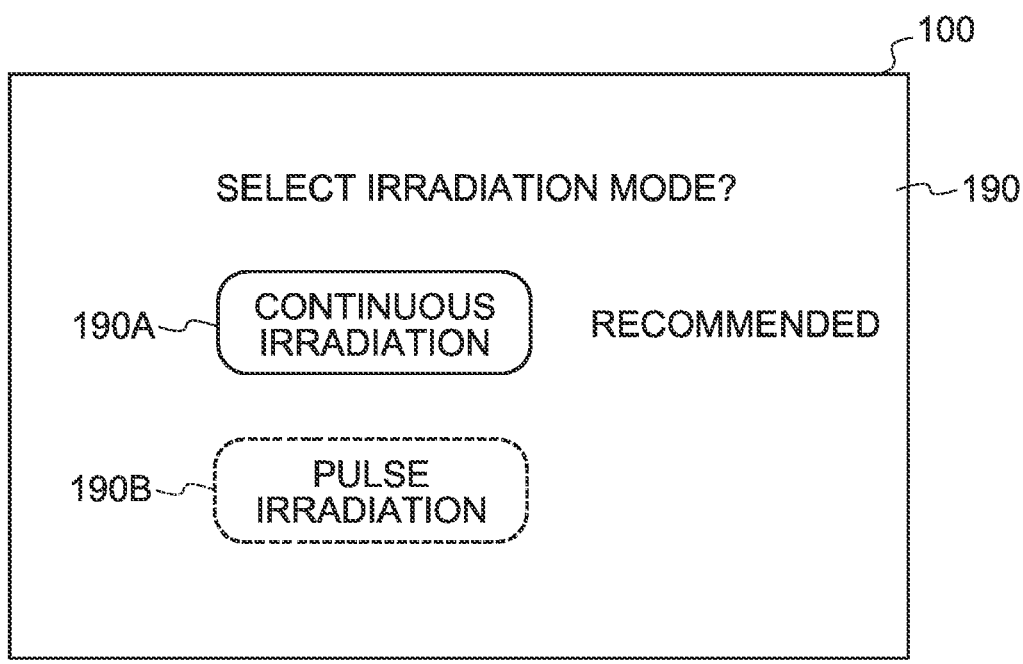

In the present exemplary embodiment, the designation screen is displayed when receiving designation (selection) of which of continuous irradiation and pulse irradiation the radiographic image capturing is to be carried out. The selection screen displays that the type of irradiation whose priority level is high is recommended, and that the type of irradiation that is prohibited cannot be selected in the selection screen. FIG. 9A illustrates an example of a selection screen 190 that is displayed on the display 100 in a case in which the priority level of pulse irradiation is low and the priority level of continuous irradiation is high. FIG. 9B illustrates an example of the selection screen 190 that is displayed on the display 100 in a case in which pulse irradiation is prohibited and the priority level of continuous irradiation is high. A button 190A that designates continuous irradiation and a button 190B that designates pulse irradiation are provided in the designation screen 190. In FIGS. 9A and 9B, a message that this type of irradiation is recommended is displayed next to the button 190A. In FIG. 9B, pulse irradiation that is prohibited is made invalid so as to not be able to be selected.

Due thereto, in accordance with the present exemplary embodiment, to the extent that the frame rate of fluoroscopic imaging is slow, the fluoroscopic imaging is carried out by irradiating radiation continuously. Therefore, fluoroscopic images having smooth motion can be captured.

In continuous irradiation, because radiation is irradiated continuously, there is no need to synchronize the timing of irradiating the radiation and the image capturing timing. However, with continuous irradiation, because radiation is irradiated also at the time of image read-out, the irradiated amount of radiation per unit time must be kept low in order to curb the amount of radiation that the subject 48 is exposed to.

Thus, with continuous irradiation, in a case in which fluoroscopic imaging is carried out at a frame rate designated by the operator, there are cases in which the minimum irradiated amount that is needed to capture radiographic images cannot be ensured.

Thus, in the present exemplary embodiment, in a case in which fluoroscopic imaging by continuous irradiation is designated by the operator, judgment is made as to whether or not the minimum irradiated amount needed for radiographic image capturing can be ensured.

Figure 10:
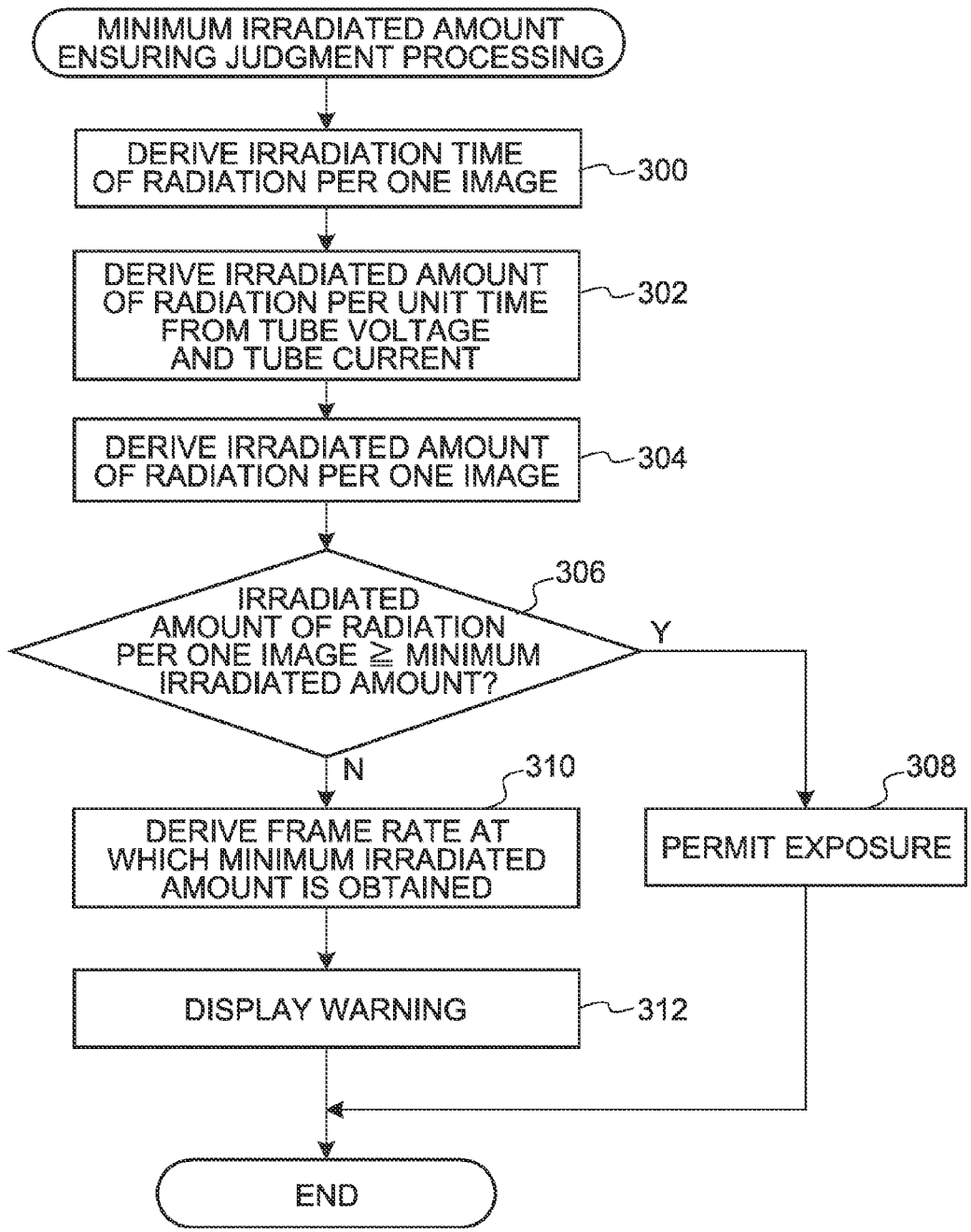
FIG. 10 is a flowchart showing the flow of a minimum irradiated amount ensuring judgment processing program relating to the exemplary embodiment.

FIG. 10 is a flowchart showing the flow of processings of a minimum irradiated amount ensuring judgment processing program that is executed by the CPU 104 relating to the present exemplary embodiment. Note that this program is stored in advance in a predetermined area of the HDD 110, and is executed when a designating operation that designates fluoroscopic imaging by continuous irradiation is carried out with respect to the operation panel 102.

In step 300 of FIG. 10, the irradiation time of the radiation per one image is derived from the frames of the fluoroscopic imaging. In the present exemplary embodiment, for example, the image read-out time that is required for reading-out one image is stored in advance in the HDD 110, and the planned image capturing time per one image is determined from the frame rate. By subtracting the image read-out time from this planned image capturing time, the irradiation time of the radiation per one image is derived.

In step 302, the irradiated amount of radiation per unit time is derived from the designated tube voltage and tube current.

In step 304, the irradiated amount of radiation per one image is derived by multiplying the irradiation time of radiation per one image, that was derived in step 300, by the irradiated amount of radiation per unit time that was derived in step 304.

In step 306, judgment is made as to whether or not the irradiated amount of radiation per one image is greater than or equal to a minimum irradiated amount. If the judgment is affirmative, the routine moves on to step 308, and, after image capturing is permitted, the present minimum irradiated amount ensuring judgment processing program ends. If the judgment is negative, the routine moves on to step 310.

In step 310, by dividing the minimum irradiated amount by the irradiated amount of radiation per unit time, the irradiation time of radiation at which the minimum irradiated amount is obtained is determined, and the frame rate at which this irradiation time is obtained is derived.

In step 312, the fact that the minimum irradiated amount needed for radiographic image capturing cannot be ensured is displayed on the display 100, and the frame rate derived in above step 310 is displayed on the display 100 as a frame rate at which the minimum irradiated amount can be ensured, and the present minimum irradiated amount ensuring judgment processing program ends.

Due thereto, in accordance with the present exemplary embodiment, warning can be given in a case in which the minimum irradiated amount that is needed for capturing radiographic images cannot be ensured.

Note that, in the minimum irradiated amount ensuring judgment processing program relating to the present exemplary embodiment, as the warning, processing is carried out to display, on the display 100 of the console 42, a display of the fact that the minimum irradiated amount that is needed cannot be ensured. However, the present exemplary embodiment is not limited to the same. For example, in addition to a form that displays, by the display 100, such information that urges caution, any other processing that can urge caution such as providing a buzzer at the console 42 and carrying out the processing of sounding the buzzer, or providing a speaker at the console 42 and carrying out the processing of issuing a voice message that urges caution from the speaker, or providing a warning lamp at the console 42 and carrying out the processing of lighting the warning lamp or causing the warning lamp to flash, or the like, or combinations thereof, may be utilized.

When the fact that the minimum irradiated amount needed for radiographic image capturing cannot be ensured is displayed on the display 100, the operator may again carry out frame rate designation. When image capturing is permitted and the display 100 displays that preparations for image capturing have been completed, the operator may carry out an image capturing instructing operation that instructs image capturing with respect to the operation panel 102 of the console 42.

When an image capturing start operation is carried out at the operation panel 102, the console 42 starts the image capturing operations shown in FIG. 11 through FIG. 14 that are described below, in accordance with which of still image capturing by continuous irradiation, still image capturing by pulse irradiation, fluoroscopic imaging by continuous irradiation, and fluoroscopic imaging by pulse irradiation has been designated.

Figure 11:
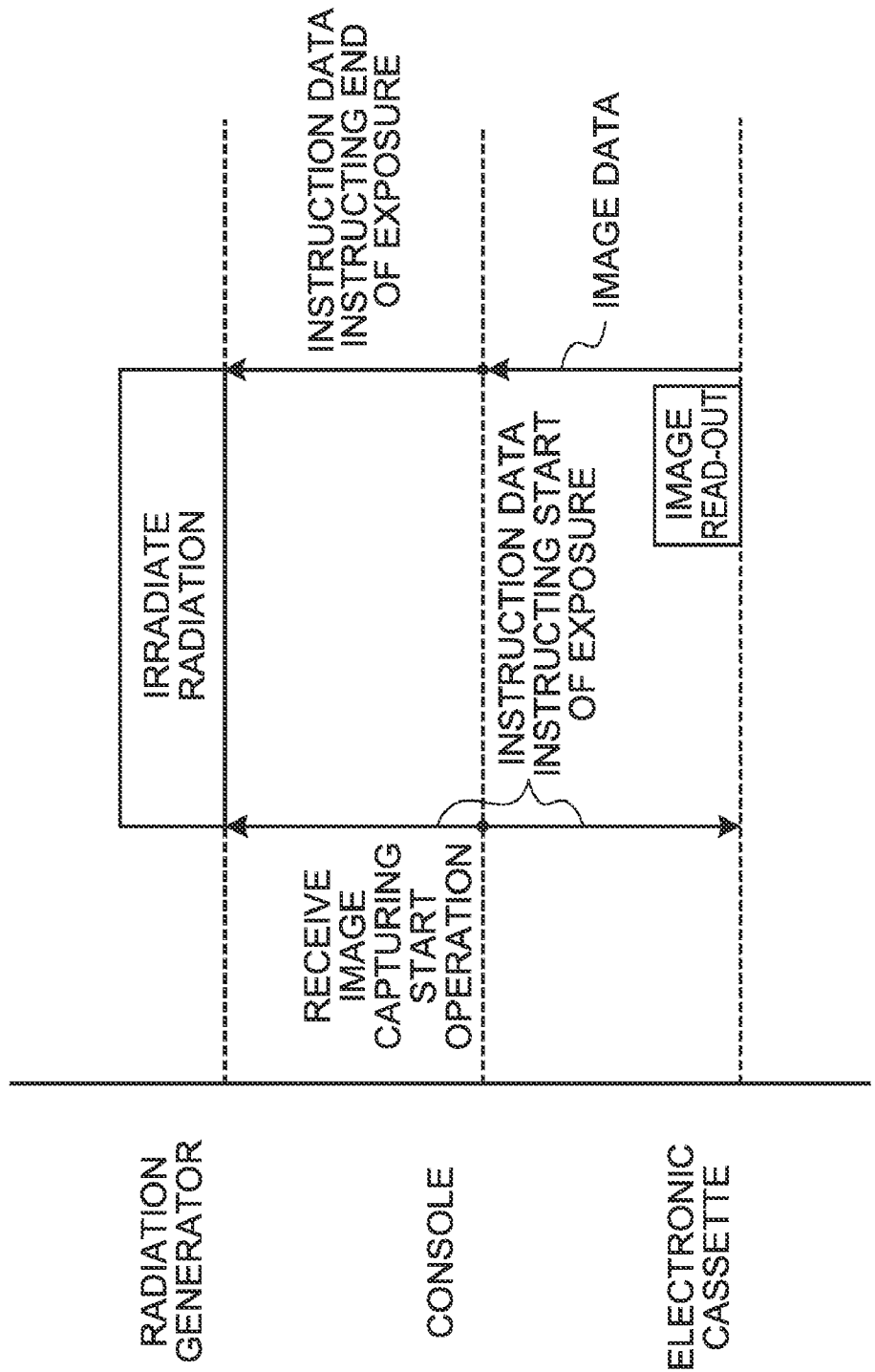
FIG. 11 is a time chart showing the flow of image capturing operations in a case in which still image capturing by continuous irradiation relating to the exemplary embodiment is selected.

FIG. 11 is a time chart showing the flow of image capturing operations in a case in which still image capturing by continuous irradiation is designated.

In a case in which an image capturing start operation is carried out at the operation panel 102, the console 42 transmits instruction information (data), that instructs the start of exposure, to the radiation generator 34 and the electronic cassette 32.

When the radiation generator 34 receives the instruction data that instructs the start of exposure, the radiation generator 34 starts generating and emitting radiation at the tube voltage and tube current corresponding to the exposure conditions received from the console 42.

After the irradiation time that is designated in the exposure conditions elapses from the receipt of the instruction data that instructs the start of exposure, the cassette controller 92 of the electronic cassette 32 controls the gate line driver 80 and causes on signals to be outputted from the gate line driver 80 to the respective gate lines 76 in order and line-by-line, and turns the respective TFTs 70, that are connected to the respective gate lines 76, on in order and line-by-line.

At the radiation detector 60, when the respective TFTs 70 that are connected to the respective gate lines 76 are turned on in order and line-by-line, the charges, that have been accumulated in the respective storage capacitors 68, flow-out in order and line-by-line to the respective data lines 78 as electric signals. The electric signals that have flowed-out to the respective data lines 78 are converted into digital image data at the signal processor 82, are stored in the image memory 90, and are transmitted to the console 42.

When the console 42 receives the image data, the console 42 transmits instruction data, that instructs the end of exposure, to the radiation generator 34, and carries out image processings that effect various types of corrections, such as shading correction and the like, on the received image data, and stores the image data after the image processing in the HDD 110.

When the radiation generator 34 receives the instruction data that instructs the end of exposure, the radiation generator 34 ends the generating and emitting of radiation.

The image data stored in the HDD 110 is displayed on the display 100 for confirmation of the captured radiographic image and the like, and is transferred to the RIS server 14 and stored in the database 14A as well. Due thereto, a doctor can carry out interpretation of the captured radiographic image, diagnosis, and the like.

Figure 12:
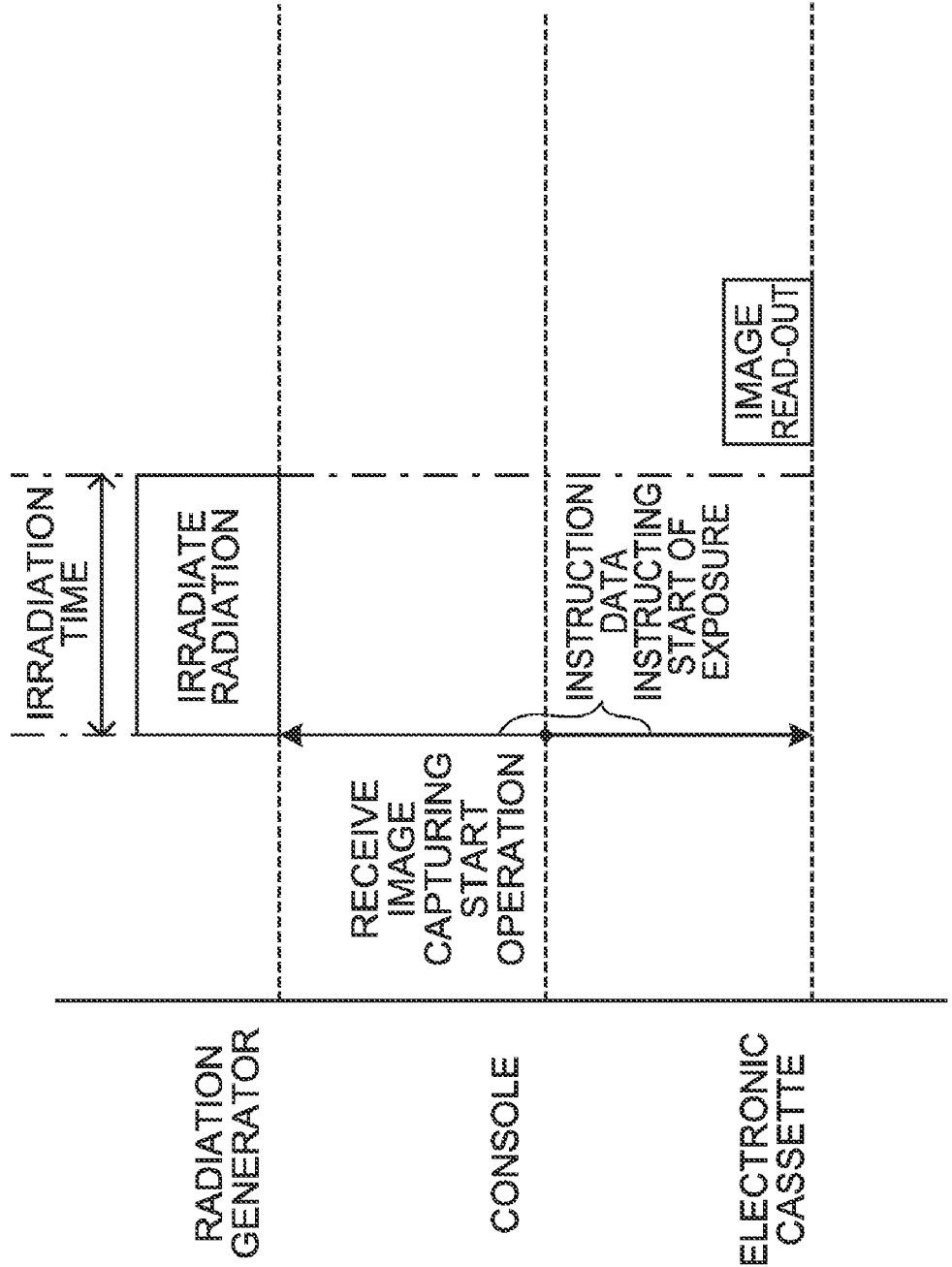
FIG. 12 is a time chart showing the flow of image capturing operations in a case in which still image capturing by pulse irradiation relating to the exemplary embodiment is selected.

FIG. 12 is a time chart showing the flow of image capturing operations in a case in which still image capturing by pulse irradiation is designated.

In a case in which an image capturing start operation is carried out at the operation panel 102, the console 42 transmits instruction data, that instructs the start of exposure, to the radiation generator 34 and the electronic cassette 32.

When the radiation generator 34 receives the instruction data that instructs the start of exposure, the radiation generator 34 generates and emits radiation at the tube voltage and tube current and for the irradiation time that correspond to the exposure conditions received from the console 42.

After the irradiation time that is designated in the exposure conditions elapses from the receipt of the instruction data that instructs the start of exposure, the cassette controller 92 of the electronic cassette 32 controls the gate line driver 80 and causes on signals to be outputted from the gate line driver 80 to the respective gate lines 76 in order and line-by-line, and turns the respective TFTs 70, that are connected to the respective gate lines 76, on in order and line-by-line.

At the radiation detector 60, when the respective TFTs 70 that are connected to the respective gate lines 76 are turned on in order and line-by-line, the charges, that have been accumulated in the respective storage capacitors 68, flow-out in order and line-by-line to the respective data lines 78 as electric signals. The electric signals that have flowed-out to the respective data lines 78 are converted into digital image data at the signal processor 82, are stored in the image memory 90, and are transmitted to the console 42. The image data transmitted to the console 42 is subjected at the console 42 to image processings that effect various types of corrections, such as shading correction and the like, and is stored in the HDD 110. The image data stored in the HDD 110 is displayed on the display 100 for confirmation of the captured radiographic image and the like, and is transferred to the RIS server 14 and stored in the database 14A as well.

Figure 13:
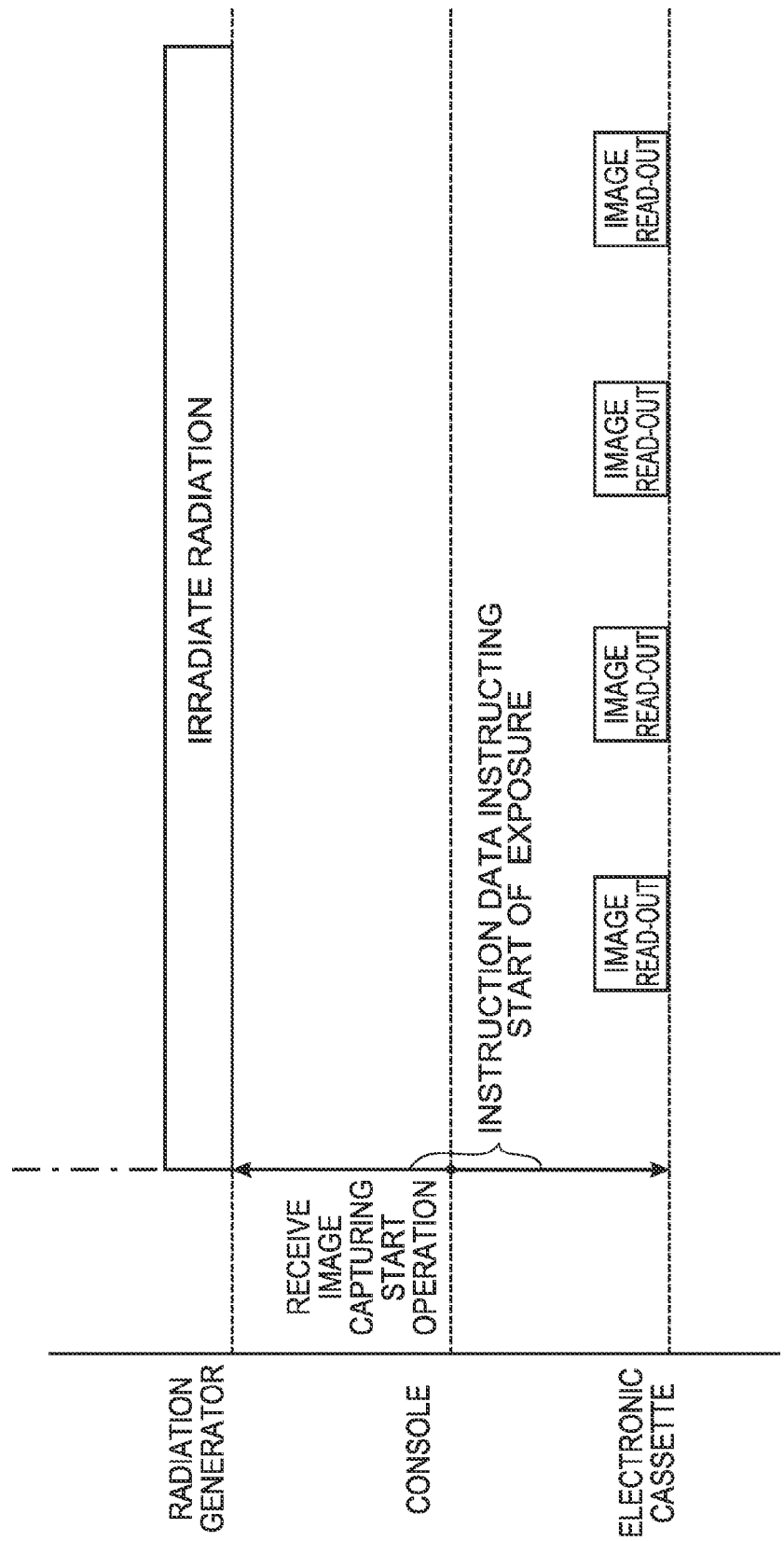
FIG. 13 is a time chart showing the flow of image capturing operations in a case in which fluoroscopic imaging by continuous irradiation relating to the exemplary embodiment is selected.

FIG. 13 is a time chart showing the flow of image capturing operations in a case in which fluoroscopic imaging by continuous irradiation is designated.

In a case in which an image capturing start operation is carried out at the operation panel 102, the console 42 transmits instruction data, that instructs the start of exposure, to the radiation generator 34 and the electronic cassette 32.

When the radiation generator 34 receives the instruction data that instructs the start of exposure, the radiation generator 34 starts irradiating radiation at the tube voltage and tube current corresponding to the exposure conditions received from the console 42.

When the cassette controller 92 of the electronic cassette 32 receives the instruction data that instructs the start of exposure, the cassette controller 92 repeatedly carries out, at a period corresponding to the designated frame rate, controlling the gate line driver 80 and causing on signals to be outputted from the gate line driver 80 to the respective gate lines 76 in order and line-by-line, and turning the respective TFTs 70, that are connected to the respective gate lines 76, on in order and line-by-line, and reading-out the images, so as to carry out reading-out of the images at the designated frame rate. The electric signals that have flowed-out to the respective data lines 78 of the radiation detector 60 are converted into digital image data at the signal processor 82, are stored in the image memory 90, and are transmitted to the console 42 by one image (frame) worth of data amount at a time. The image data that are transmitted to the console 42 are subjected, at the console 42, to image processings that effect various types of corrections, such as shading correction and the like, and are stored in the HDD 110. The image data stored in the HDD 110 is displayed on the display 100 for confirmation of the captured radiographic images and the like, and is transferred to the RIS server 14 and stored in the database 14A as well.

When an image capturing end operation is carried out at the operation panel 102, the console 42 transmits instruction data that instructs the end of exposure to the radiation generator 34 and the electronic cassette 32. Due thereto, the radiation source 130 stops irradiation of the radiation, and the electronic cassette 32 ends the reading-out of images.

Figure 14:
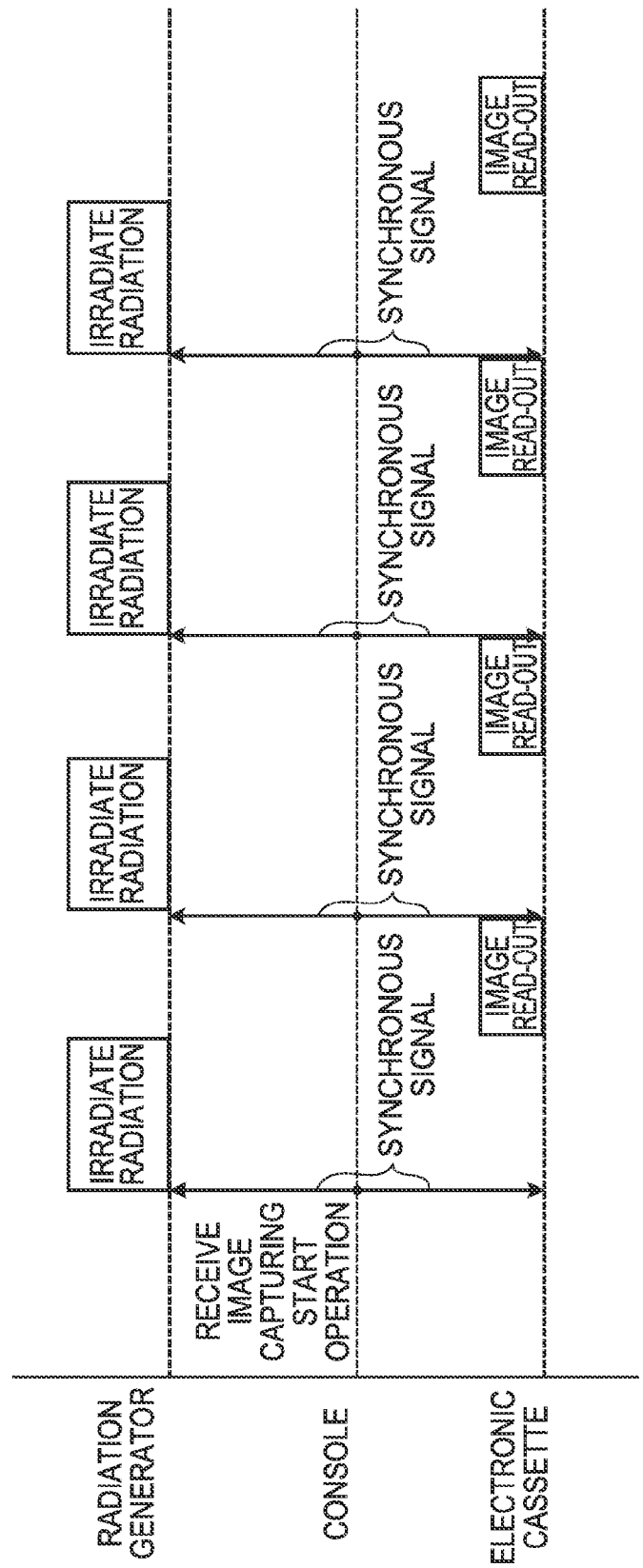
FIG. 14 is a time chart showing the flow of image capturing operations in a case in which fluoroscopic imaging by pulse irradiation relating to the exemplary embodiment is selected.

FIG. 14 is a time chart showing the flow of image capturing operations in a case in which fluoroscopic imaging by pulse irradiation is designated.

The console 42 transmits, to the radiation generator 34 and the electronic cassette 32, a synchronous signal at a period corresponding to the designated frame rate.

Each time the radiation generator 34 receives the synchronous signal, the radiation generator 34 generates and emits radiation at the tube voltage and tube current and for the irradiation time that correspond to the exposure conditions received from the console 42.

After the irradiation time that is designated in the exposure conditions elapses from the receipt of the synchronous signal, the cassette controller 92 of the electronic cassette 32 controls the gate line driver 80 and causes on signals to be outputted from the gate line driver 80 to the respective gate lines 76 in order and line-by-line, and turns the respective TFTs 70, that are connected to the respective gate lines 76, on in order and line-by-line, and reads-out the image. The electric signals that have flowed-out to the respective data lines 78 of the radiation detector 60 are converted into digital image data at the signal processor 82, are stored in the image memory 90, and are transmitted to the console 42 by one image (frame) worth of data amount at a time. The image data that are transmitted to the console 42 are subjected, at the console 42, to image processings that effect various types of corrections, such as shading correction and the like, and are stored in the HDD 110. The image data stored in the HDD 110 is displayed on the display 100 for confirmation of the captured radiographic images and the like, and is transferred to the RIS server 14 and stored in the database 14A as well.

When an image capturing end operation is carried out at the operation panel 102, the console 42 transmits instruction data that instructs the end of exposure to the radiation generator 34 and the electronic cassette 32. Due thereto, the radiation source 130 stops irradiation of the radiation, and the electronic cassette 32 ends the reading-out of images.

In cases of carrying out still image capturing and fluoroscopic imaging by continuous irradiation, the radiation amount that is irradiated per unit time is reduced as compared with the case of pulse irradiation. Therefore, in cases in which still image capturing and fluoroscopic imaging are carried out by continuous irradiation, the cassette controller 92 may carry out at least one of extending the charge accumulating time periods at the respective pixels 74, increasing the gain amount of the operation amplifier 84A, and image processing for making plural adjacent pixels 74 be one pixel.

Due thereto, good images can be obtained even in cases in which fluoroscopic imaging is carried out by continuous irradiation and the irradiated radiation amount per unit time is lowered.

There are cases in which, at the radiation generator 34 relating to the present exemplary embodiment, shaking arises due to some object contacting or colliding with the radiation source 130 during image capturing, and capturing of radiographic images fails.

Thus, at the radiation generator 34 relating to the present exemplary embodiment, in order to prevent failure in capturing radiographic images due to some object contacting or colliding with the radiation source 130 during image capturing, accelerations in directions of three axes are detected by the acceleration sensor 156 each predetermined time period (each 0.1 seconds in the present exemplary embodiment), and acceleration information (data), that expresses the detected accelerations in the three axial directions, is transmitted to the console 42.

At the console 42, in order to judge whether or not shaking has arisen at the radiation source 130 during image capturing, shaking threshold values are stored in advance in the HDD 110, and a judgment is made as to whether or not shaking has arisen by comparing the accelerations in the three axial directions with the threshold values. In the present exemplary embodiment, two shaking threshold values (a first shaking threshold value and a second shaking threshold value) are stored. The first shaking threshold value is an amount of shaking of an extent such that the offset in the irradiated region of the radiation from the radiation generator 34 is small and image capturing does not fail. The second shaking threshold value is an amount of shaking of an extent such that the irradiated region of the radiation from the radiation generator 34 is greatly offset, and image capturing fails.

When the console 42 receives the acceleration information from the radiation generator 34, the console 42 executes erroneous irradiation preventing processing.

Operation of the console 42 at the time of executing the erroneous irradiation preventing processing is described next with reference to FIG. 15. FIG. 15 is a flowchart showing the flow of an erroneous irradiation preventing processing program that is executed as interruption processing by the CPU 104 of the console 42 at this time. This program also is stored in advance in a predetermined area of the ROM 106.

In step 400 of FIG. 15, a judgment is made as to whether or not any of the accelerations in the three axial directions that are expressed by the received acceleration data is greater than or equal to the first shaking threshold value. If the judgment is negative, the present erroneous irradiation preventing processing program ends, whereas if the judgment is affirmative, the routine proceeds to step 402.

In step 402, a judgment is made as to whether or not any of the accelerations in the three axial directions that are expressed by the received acceleration data is greater than or equal to the second shaking threshold value. If the judgment is negative, the routine moves on to step 404, whereas if the judgment is affirmative, the routine proceeds to step 406.

In step 404, a predetermined warning is started, and thereafter, the present erroneous irradiation preventing processing program ends.

In the erroneous irradiation preventing processing program relating to the present exemplary embodiment, as the aforementioned predetermined warning, processing is carried out to display, on the display 100 of the console 42, a warning screen that urges caution. However, the present exemplary embodiment is not limited to the same. For example, in addition to the form that displays, by the display 100, such information that urges caution, any other processing that can urge caution such as providing a buzzer at the console 42 and carrying out the processing of sounding the buzzer, or providing a speaker at the console 42 and carrying out the processing of issuing a voice message that urges caution from the speaker, or providing a warning lamp at the console 42 and carrying out the processing of lighting the warning lamp or causing the warning lamp to flash, or the like, or combinations thereof, may be utilized.

In step 406, after a predetermined irradiation prohibiting processing is executed, the present erroneous irradiation preventing processing program ends.

In the erroneous irradiation preventing processing program relating to the present exemplary embodiment, as the aforementioned irradiation prohibiting processing, processing that stops irradiation of the radiation X from the radiation source 130 is carried out with respect to the radiation generator 34, and processing for displaying, by the display 100 of the console 42, a presenting screen that expresses that irradiation of radiation is prohibited is carried out, and thereafter, processing that forcibly ends execution of the above-described radiographic image capturing processing program is carried out. Further, in the erroneous irradiation preventing processing program relating to the present exemplary embodiment, as the aforementioned processing that stops irradiation of the radiation X, processing that transmits, to the radiation generator 34, instruction data for forcibly cutting-off the supply path of electric power for driving to the radiation source 130, is carried out. However, the exemplary embodiment is not limited to these, and other processings that can stop the irradiation of the radiation X by the radiation source 130, such as, for example, processing that transmits to the radiation generator 34 instruction data to stop irradiation of the radiation X by the radiation source 130, or the like, may be applied.

Due thereto, in accordance with the present exemplary embodiment, even in a case in which some object contacts or collides with the radiation source 130 and the radiation source 130 shakes, control for preventing irradiation of radiation from the radiation source is executed. Therefore, failure of radiographic image capturing and deterioration in the quality of images obtained by capturing, that are caused by contact of an object during image capturing, can be prevented.

The present invention has been described above by using an exemplary embodiment, but the technical scope of the present invention is not limited to the scope described by the above exemplary embodiment. Various changes and improvements can be made to the exemplary embodiment within a scope that does not deviate from the gist of the present invention, and forms to which such changes and improvements are made also are included within the technical scope of the present invention.

The above exemplary embodiment does not limit the inventions recited in the claims, and it is not necessarily the case that all of the combinations of features described in the exemplary embodiment are essential to the means of the present invention for solving the problems of the conventional art. Inventions of various stages are included in the above exemplary embodiment, and various inventions can be extracted by appropriately combining plural constituent features that are disclosed. Even if some of the constituent features are removed from all of the constituent features that are illustrated in the exemplary embodiment, such structures from which some constituent features are removed can be extracted as inventions provided that the effects of the present invention are obtained thereby.

In the above exemplary embodiment, description is given of a case in which, when shaking arises, processing that prohibits the irradiation of the radiation X is carried out by the console 42 with respect to the radiation source 130, but the exemplary embodiment is not limited to this. For example, the radiation generator 34 itself may execute such processing. An embodiment in which the erroneous irradiation preventing processing program (see FIG. 15) is executed by the radiation source controller 134 of the radiation generator 34 can be given as an example in this case. In this case, processings for transmitting and receiving distance information are not carried out. In this case as well, effects that are similar to those of the above-described exemplary embodiment can be achieved.

Further, the exemplary embodiment describes a case in which a structure having a C arm is used as the radiation generator 34, but the exemplary embodiment is not limited to the same. For example, there may be a form in which a movable radiation generator that does not have a C arm, such as that disclosed in JP-A No. 2005-323673 for example, is applied. In this case as well, effects that are similar to those of the above-described exemplary embodiment can be achieved.

Although the above exemplary embodiment describes a case in which a movable structure is used as the radiation generator 34, the exemplary embodiment is not limited to the same. For example, a structure in which only the radiation source 130 is moved by a moving mechanism in the radiographic image capturing room 44 may be applied as the radiation generator. In this case, the structure can be applied in the same way as in the above-described exemplary embodiment by deriving the distances of another object with respect to the radiation source 130 and the moving mechanism. Also in this case, effects that are similar to those of the above-described exemplary embodiment can be achieved.

The exemplary embodiment describes a case in which the electronic cassette 32 is used independently without being attached to the radiation generator 34, but the exemplary embodiment is not limited to the same. For example, there may be a form in which the electronic cassette 32 is used in a state of being attached to the attachment structure 142 of the radiation generator 34. Effects that are similar to those of the above-described exemplary embodiment can be achieved in this case as well.

In the above exemplary embodiment, a case is described in which, by the minimum irradiated amount ensuring judgment processing program (FIG. 10), a judgment is made as to whether or not the minimum irradiated amount needed for capturing of radiographic images can be ensured, and, in a case in which the minimum irradiated amount cannot be ensured, warning is given by displaying on the display 100 the fact that the minimum irradiated amount cannot be ensured. However, the exemplary embodiment is not limited to the same, and for example, the frame rate may be automatically switched to a frame rate at which the minimum irradiated amount can be ensured.

Figure 16A:
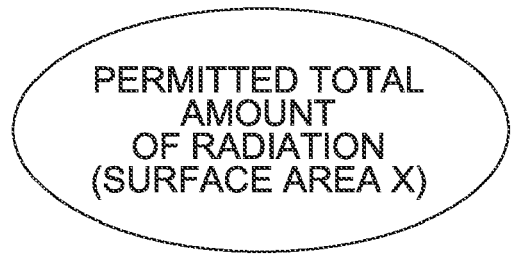
FIGS. 16A through 16C are schematic drawings showing the relationship between a permitted total amount of radiation, image capturing time, and irradiated amount of radiation per unit time, relating to another exemplary embodiment.
Figure 16B:
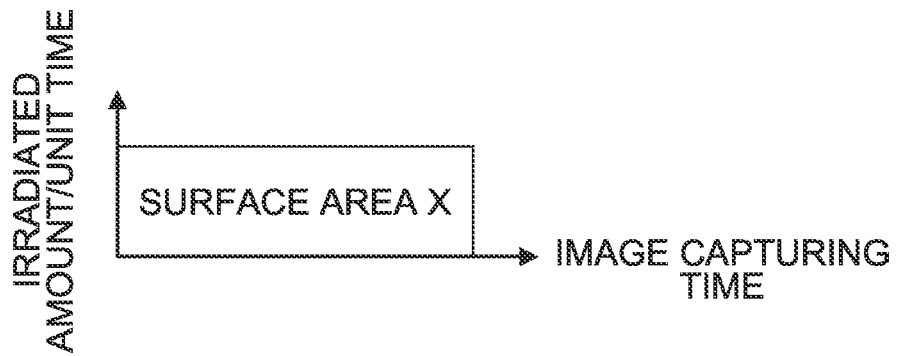
Figure 16C:
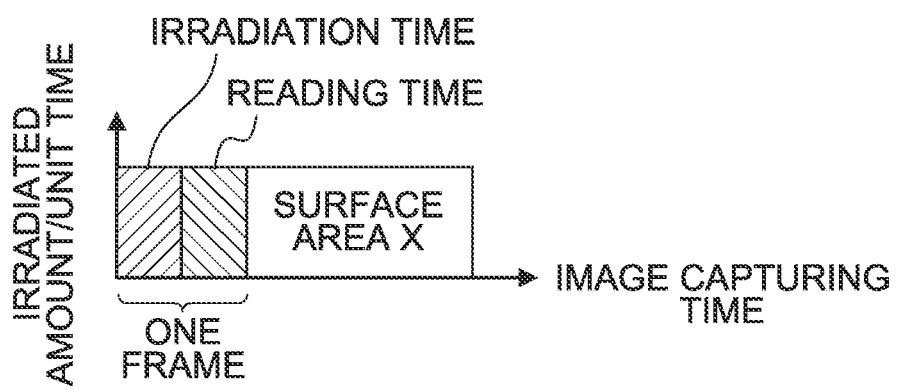

The exemplary embodiment describes a case in which, in cases in which fluoroscopic imaging is designated as the image capturing mode, exposure conditions such as the frame rate, the tube voltage, the tube current and the like are designated to the operation panel 102. However, the exemplary embodiment is not limited to the same. For example, the frame rate, the total amount of radiation that is permitted to be irradiated at the time of fluoroscopic imaging, and the planned image capturing time may be designated. Further, data expressing the total amount of radiation that is permitted to be irradiated for each imaged region may be stored in advance in the HDD 110, and, when the imaged region is designated, the total amount of radiation that corresponds to the designated imaged region may be obtained from the stored data. In fluoroscopic imaging by continuous irradiation, in cases in which the fluoroscopic imaging is carried out at a designated frame rate, there are cases in which the minimum irradiated amount that is needed for capturing of the radiographic images cannot be ensured. Therefore, as shown in FIG. 16A through 16C, it can be judged whether or not fluoroscopic imaging by continuous irradiation is possible by dividing the total amount of radiation that is permitted (FIG. 16A) by the planned image capturing time, and deriving the irradiated amount of radiation per unit time (FIG. 16B), and judging whether the minimum irradiated amount can be ensured in the irradiation time of the radiation per one image (FIG. 16C).

Figure 17:
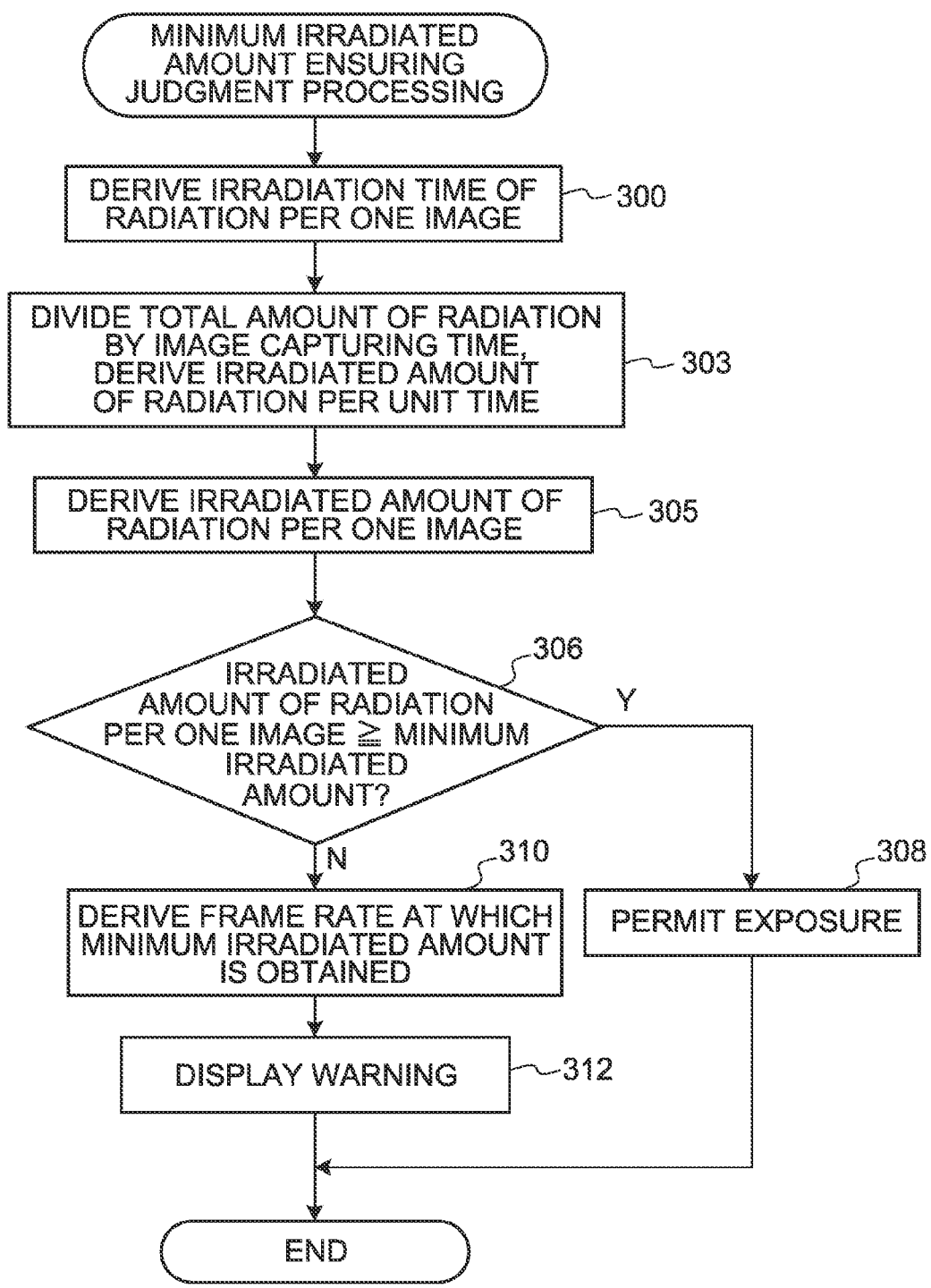
FIG. 17 is a flowchart showing the flow of a minimum irradiated amount ensuring judgment processing program relating to the other exemplary embodiment.

An example of a minimum irradiated amount ensuring judgment processing program is shown in FIG. 17. Note that portions that are the same as in the above-described exemplary embodiment (FIG. 10) are denoted by the same reference numerals, and description thereof is omitted.

In step 303, the irradiated amount of radiation per unit time is derived by dividing the permitted total amount of radiation by the planned image capturing time.

In step 305, the irradiated amount of radiation per one image is derived by multiplying the irradiation time of the radiation per one image, that was derived in step 300, by the irradiated amount of radiation per unit time that was derived in step 303.

Note that, in this case as well, in cases in which the minimum irradiated amount cannot be ensured, the frame rate may be switched to a frame rate at which the minimum irradiated amount per one image is obtained.

Although the above exemplary embodiment describes a case in which control that prohibits the irradiation of radiation is applied as the control for preventing irradiation of radiation, the exemplary embodiment is not limited to the same. For example, control that delays the start timing of the irradiation of the radiation, control that reduces the irradiated amount of the radiation, or the like may be applied. In such cases as well, effects that are similar to those of the above-described exemplary embodiment can be achieved.

The above exemplary embodiment describes a case in which the acceleration sensor 156 is provided in a vicinity of the radiation source 130, but the exemplary embodiment is not limited to the same. For example, the acceleration sensor 156 may be provided at the radiation source 130 itself. Effects that are similar to those of the above-described exemplary embodiment can be achieved in this case as well.

The detecting means that detects the shaking is not limited to the acceleration sensor 156, and an azimuth sensor that detects changes in the azimuth may be applied and the shaking may be detected from the changes in the azimuth. Alternately, encoders may be incorporated into the wheel 154 portions of the radiation generator 34 or the respective movable portions of the radiation generator 34, and shaking may be detected from the amounts of movement of the wheels 154 or the C arm 140 by using the encoders. Further, a camera such as a visible light camera, an infrared ray camera or the like may be used. In this case, it is not absolutely necessary for the camera to be provided at the radiation generator 34, and, for example, the camera may be provided at the ceiling or the floor of the radiographic image capturing room 44. An example of the method for deriving the distance between the radiation generator 34 and another object in this case is a method applying a technique of providing the camera at the same position as the acceleration sensor 156 relating to the present exemplary embodiment, and continuously capturing a region that includes the surroundings of the radiation generator 34 by using the camera, and detecting changes in the image obtained by the image capturing.

In addition, the structure of the RIS 10 (see FIG. 1), the structures of the radiographic image capturing room and the radiation generator 34 (see FIG. 2), the structure of the electronic cassette 32 (see FIG. 3), and the structure of the image capturing system 18 (see FIG. 4) that are described in the above exemplary embodiment are examples. Unnecessary portions may be deleted therefrom, new portions may be added thereto, and the states of connection and the like may changed within a scope that does not deviate from the gist of the present invention.

Further, the flows of the processings of the various types of programs described in the above exemplary embodiment (refer to FIG. 7, FIG. 10, FIG. 15, FIG. 17) also are examples. Unnecessary steps thereof may be deleted therefrom, new steps may be added thereto, or the order of the processings thereof may be rearranged within a scope that does not deviate from the gist of the present invention.

What is claimed is:

1. A radiographic image capturing system comprising:
a radiographic image capturing device that is capable of performing fluoroscopic imaging, and that carries out capture of radiographic images continuously;
a radiation irradiating device that performs continuous irradiation or pulse irradiation with respect to the radiographic image capturing device at a time of fluoroscopic imaging; and
a control device having a controller that affects control such that, in a case in which a frame rate of fluoroscopic imaging is low, the radiation irradiating device performs fluoroscopic imaging by continuous irradiation with respect to the radiographic image capturing device.

2. The radiographic image capturing system of claim 1, wherein
the control device further comprises a selection section that selects whether the radiation irradiating device performs pulse irradiation or continuous irradiation, and
in a case in which a frame rate of fluoroscopic imaging is less than or equal to a first frame rate threshold value, the controller recommends continuous irradiation rather than pulse irradiation to the selection section, and, in a case in which the frame rate of fluoroscopic imaging is less than or equal to a second frame rate threshold value that is lower than the first frame rate threshold value, the controller prohibits selection of pulse irradiation to the selection section.

3. The radiographic image capturing system of claim 2, wherein the first frame rate threshold value is from 15 fps to 60 fps, and the second frame rate threshold value is from 5 fps to less than the first frame rate threshold value.

4. The radiographic image capturing system of claim 3, wherein the first frame rate threshold value is 30 fps, and the second frame rate threshold value is 15 fps.

5. The radiographic image capturing system of claim 1, wherein the controller derives an irradiated amount of radiation per one image from an irradiation time of radiation per one image at a frame rate of fluoroscopic imaging and an irradiated amount of radiation per unit time from the radiation irradiating device, and, in a case in which the derived irradiated amount of radiation per one image is less than a minimum irradiated amount that is needed for capture of radiographic images, the controller issues a warning or changes the frame rate to a frame rate at which a minimum irradiated amount per one image is obtained.

6. The radiographic image capturing system of claim 5, wherein the controller derives the irradiated amount of radiation per unit time from the radiation irradiating device by dividing a total amount of radiation permitted for an imaged region, that is an object of image capture, by a planned image capture time.

7. The radiographic image capturing system of claim 1, wherein
the radiographic image capturing device is further capable of performing still image capture, and
in a case in which still image capture is to be performed, the controller sets a priority level of pulse irradiation so as to be higher than a priority level of continuous irradiation.

8. The radiographic image capturing system of claim 1, wherein the radiation irradiating device performs continuous irradiation with a smaller radiation amount per unit time than in a case in which the radiation irradiating device performs pulse irradiation.

9. The radiographic image capturing system of claim 8, wherein the radiographic image capturing device comprises:

a radiation detector at which a plurality of pixels, that generate charge as a result of radiation being irradiated thereon and that accumulate the charge, are provided in a two-dimensional form, and that outputs the charge accumulated at the respective pixels as an electric signal;
an amplifier that amplifies the electric signal output from the radiation detector; and
an image capturing device controller that, in a case in which continuous irradiation is performed, carries out at least one of extending a charge accumulating time at the respective pixels so as to be longer than in pulse irradiation, increasing a gain amount of the amplifier so as to be greater than in pulse irradiation, and image processing that combines a plurality of adjacent pixels as one pixel.

10. The radiographic image capturing system of claim 1, further comprising a detecting section that detects shaking of the radiation irradiating device,
wherein, in a case in which a shaking amount of the radiation irradiating device detected by the detecting section during fluoroscopic imaging is greater than or equal to a first shaking threshold value, the controller issues a warning, and, in a case in which the shaking amount is greater than or equal to a second shaking threshold value that is greater than the first shaking threshold value, the controller stops irradiation of radiation from the radiation irradiating device.

11. The radiographic image capturing system of claim 10, wherein the controller issues the warning and stops irradiation of radiation in a case in which the detecting section detects shaking of the radiation detection device during fluoroscopic imaging with continuous irradiation.

* * * * *